United States Patent [19]
Siiman et al.

[11] Patent Number: 5,945,293
[45] Date of Patent: Aug. 31, 1999

[54] PROTEIN-COLLOIDAL METAL-AMINODEXTRAN COATED PARTICLE AND METHODS OF PREPARATION AND USE

[75] Inventors: Olavi Siiman, Davie; Kristie Gordon, Coral Gables; Carlos M. Rodriguez, Miami; Alexander Burshteyn, Hialeah; John A. Maples, Miami Shores, all of Fla.; James Keller Whitesell, Austin, Tex.

[73] Assignee: Coulter International Corp., Miami, Fla.

[21] Appl. No.: 08/947,811

[22] Filed: Oct. 9, 1997

[51] Int. Cl.⁶ ..................................................... G01N 33/53
[52] U.S. Cl. .......................... 435/7.24; 435/7.1; 436/523; 436/525; 436/534; 428/402; 428/403
[58] Field of Search ........................... 435/7.1, 7.2, 7.21, 435/7.24; 436/172, 518, 523, 524, 525, 526, 534, 548; 428/402, 403

[56] References Cited

U.S. PATENT DOCUMENTS

| | | |
|---|---|---|
| 5,125,737 | 6/1992 | Rodriguez et al. . |
| 5,223,398 | 6/1993 | Kortright et al. . |
| 5,231,005 | 7/1993 | Russell et al. . |
| 5,248,772 | 9/1993 | Siiman et al. . |
| 5,466,609 | 11/1995 | Siiman et al. . |
| 5,492,833 | 2/1996 | Rodriguez et al. . |
| 5,527,713 | 6/1996 | Bolton et al. . |
| 5,552,086 | 9/1996 | Siiman et al. . |
| 5,639,620 | 6/1997 | Siiman et al. . |

FOREIGN PATENT DOCUMENTS

| | | |
|---|---|---|
| 1561042 | 2/1980 | United Kingdom . |
| WO 92/09682 | 6/1992 | WIPO . |

OTHER PUBLICATIONS

*Flow Cytometry and Sorting*, p. 371, edited by Melamed, Mullaney, and Mendelsohn, 1979, John Wiley & Sons, N.Y., N.Y.
C.F. Bohren and D.F. Huffman, *Absorption and Scattering of Light by Small Beads*, Wiley–Interscience, New York, 369–374 (1983).
R.M. Böhmer, et al., *Cytometry*, 5,543–546 (1984).
R. Festin, et al., *J. Immunol. Methods*, 101:23–28 (1987).
B.J. Messinger, et al., *Phys. Rev. B*, 24, 649–657 (1981).
P.K. Horan and L.L. Wheeless, Jr., *Science*, 198:149–157 (1977).
J.K. Whitesell and H.K. Chang, *Science*, 261:73–76 (1993).
Pierce Protein Conjugation Catalog, p. 14, exact date unkown, circa late 80'.

*Primary Examiner*—Jeffrey Stucker
*Attorney, Agent, or Firm*—Mary E. Bak; Warren W. Kurz

[57] ABSTRACT

A stable colloidal particle comprises a colloidal-sized core substrate having amine-reactive functional groups thereon with an aminodextran coating over its peripheral surface and a layer of colloidal-sized metallic solid overlaying the aminodextran coating. A linker comprising aminotrithiolate attached to the metallic solid has a free amino group to which a protein is attached by covalent bonding to the free amino group. Such novel particles are useful in flow cytometry, particularly useful in the simultaneous analyses of subpopulations of leukocytes. Methods of preparation of such particles, as well as methods of use are provided. These conjugates enable the simultaneous analyses of at least two different mutually exclusive subsets of white blood cells, based on the binding affinity of the conjugated protein.

32 Claims, 28 Drawing Sheets

Whole Blood

10 μL

2 μL

20 μL

5 μL

40 μL

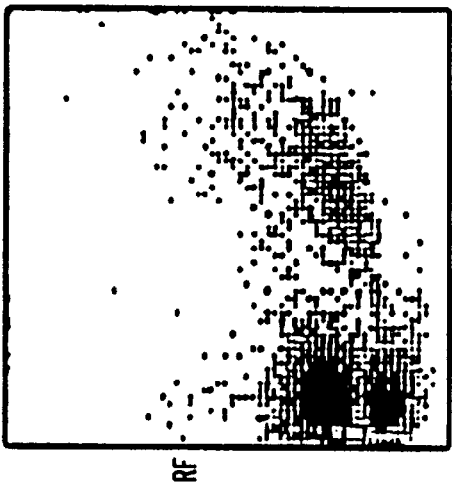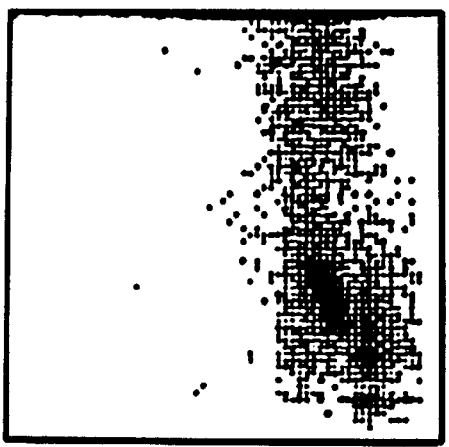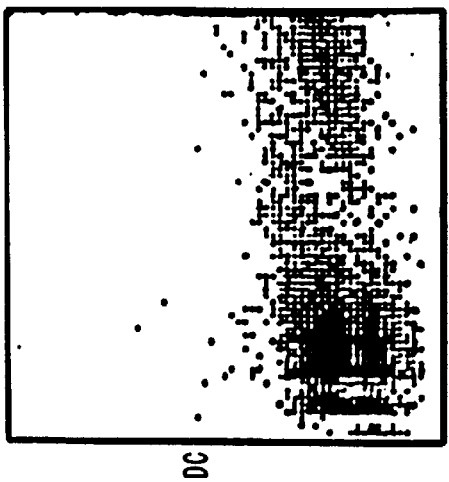

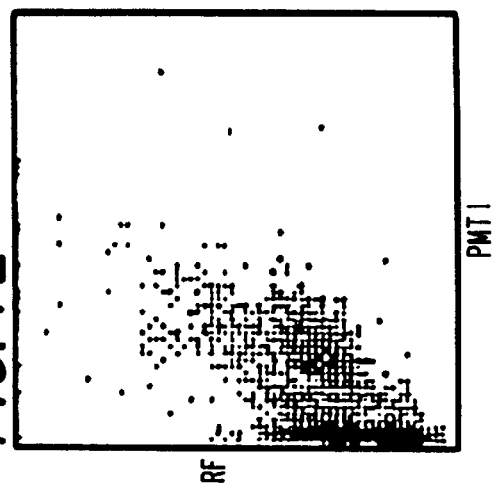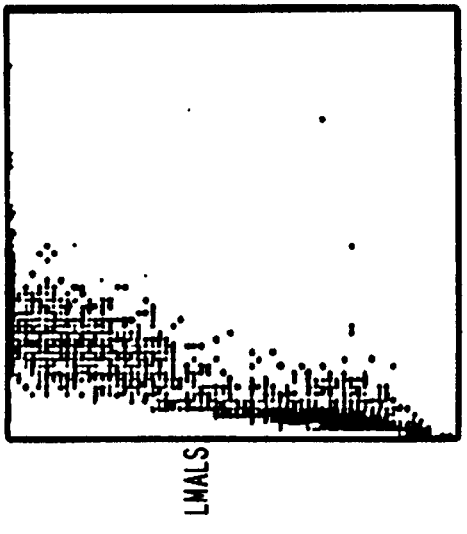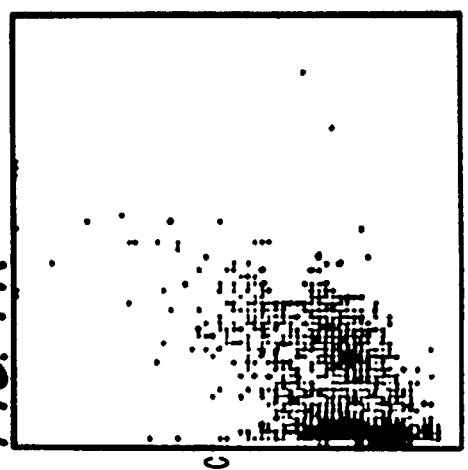

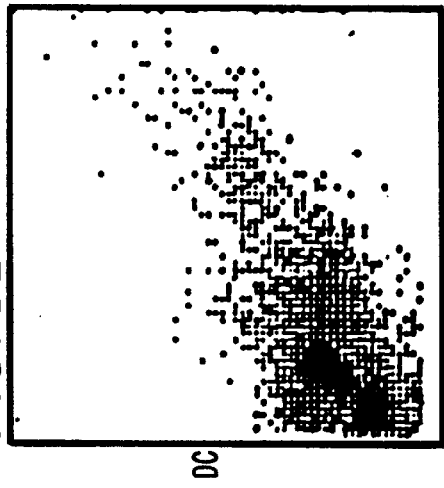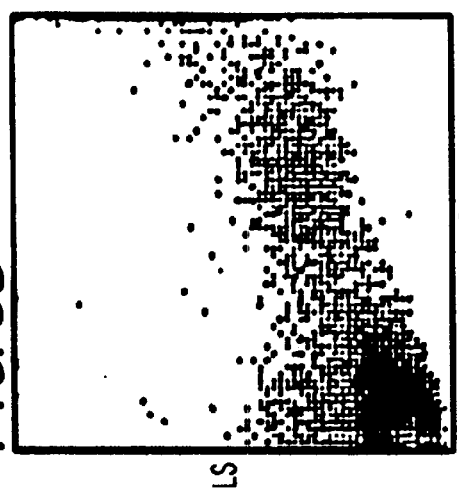

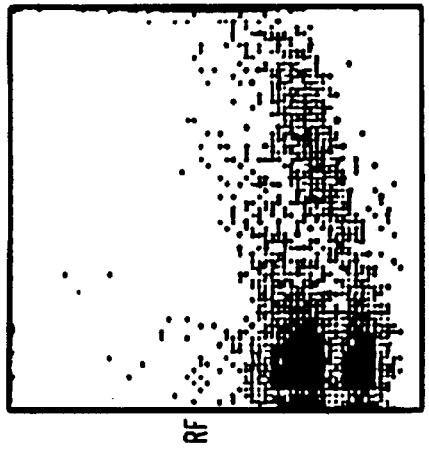
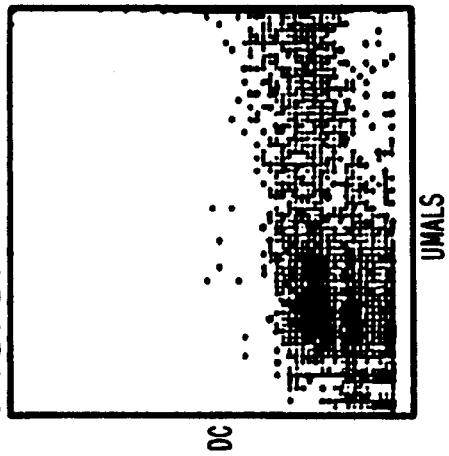
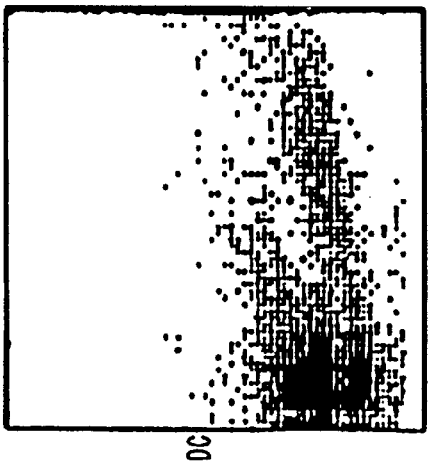
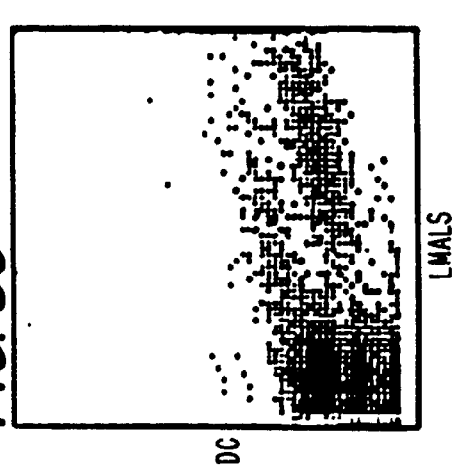

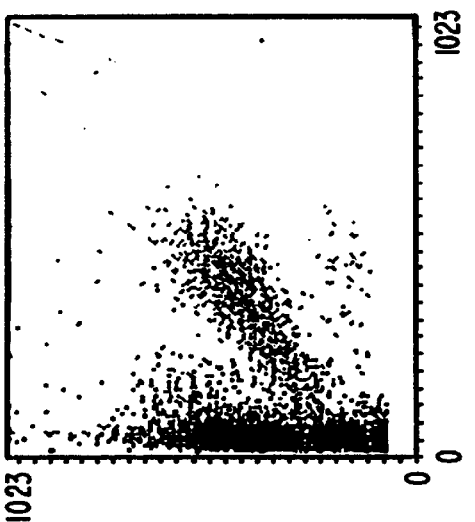
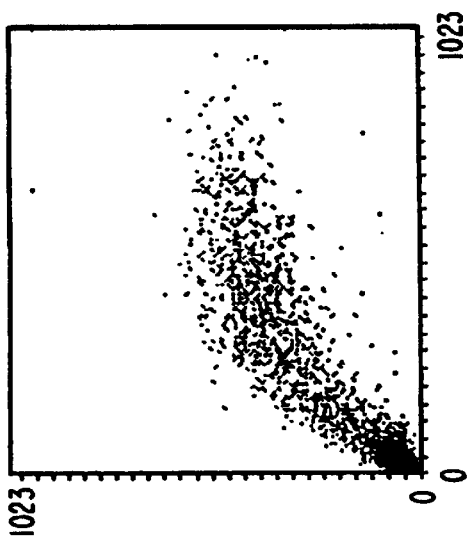
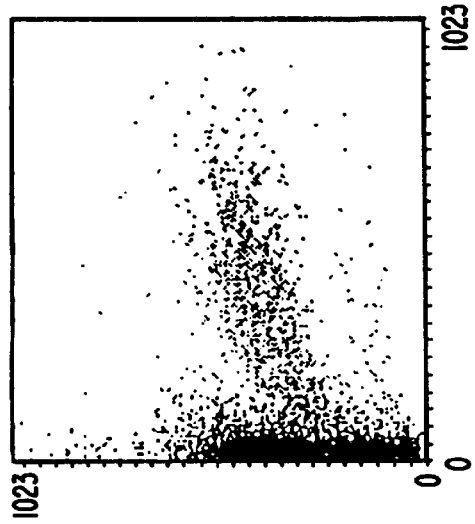

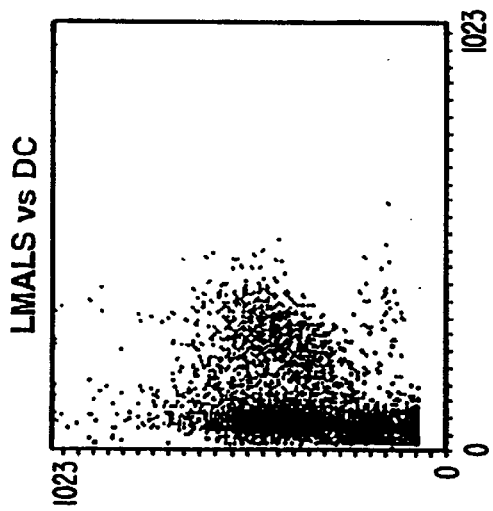
FIG. 9F LMALS vs DC
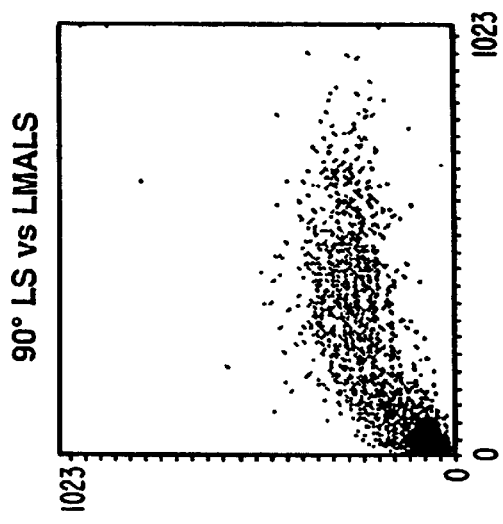
FIG. 9E 90° LS vs LMALS
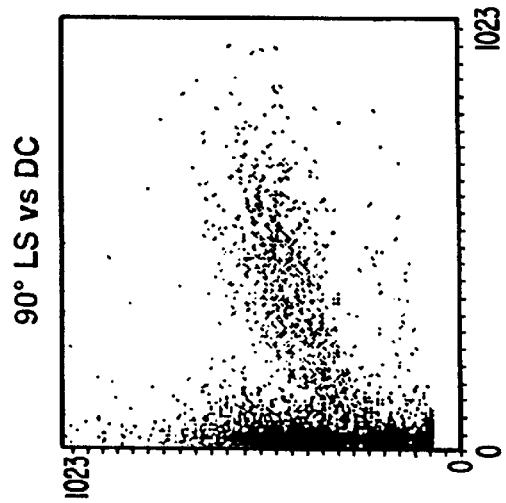
FIG. 9D 90° LS vs DC

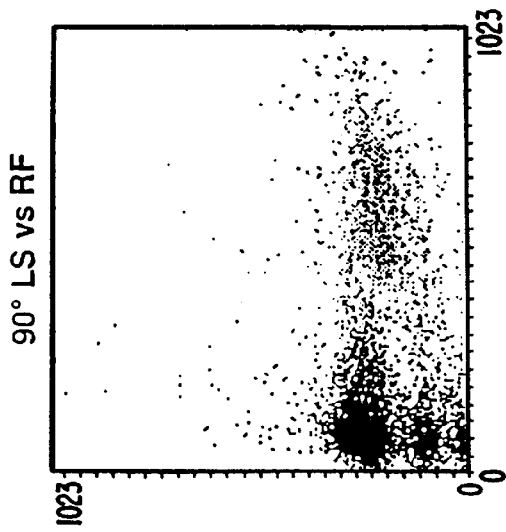
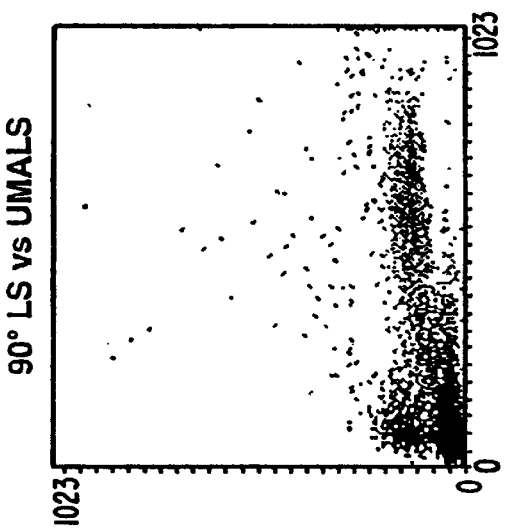
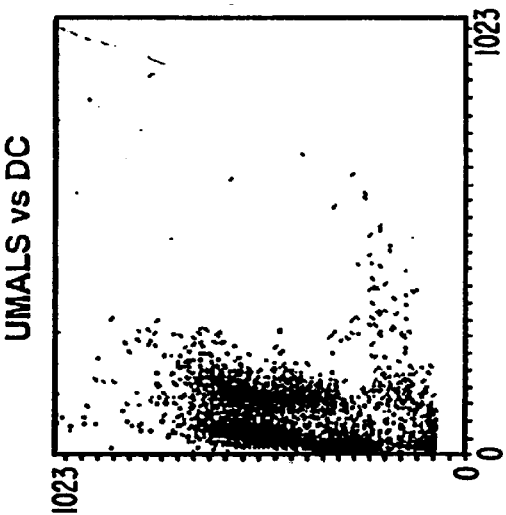

90° LS vs DC

90° LS vs LMALS

LMALS vs DC

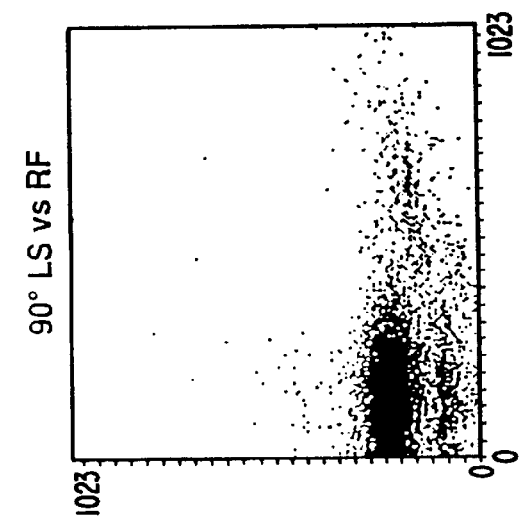
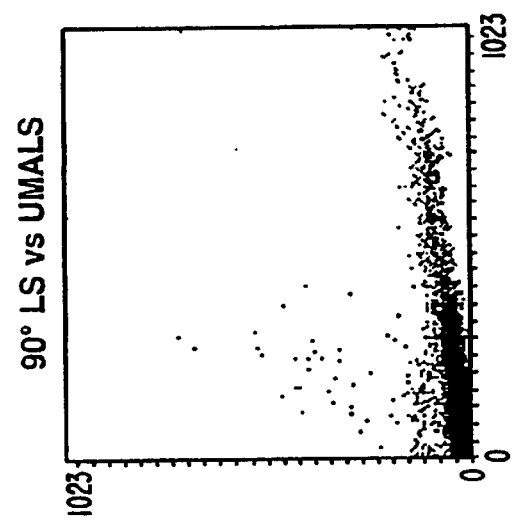
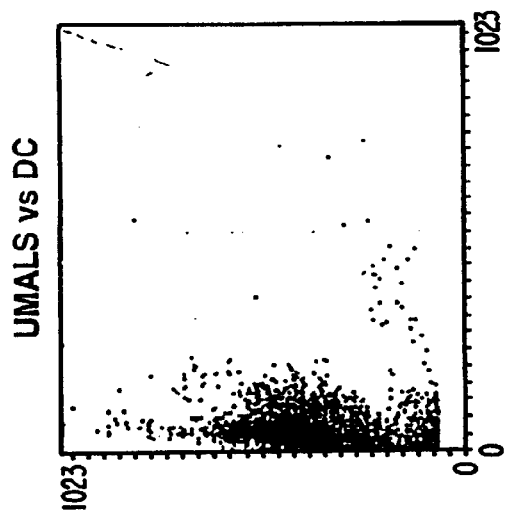

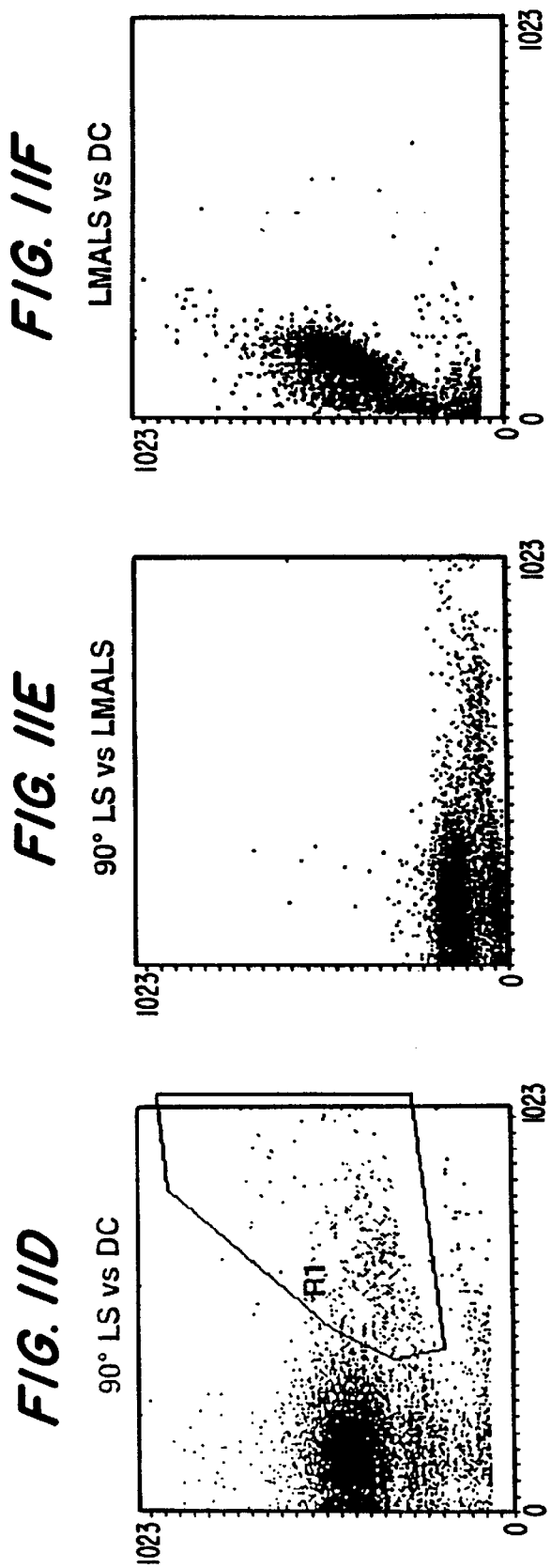

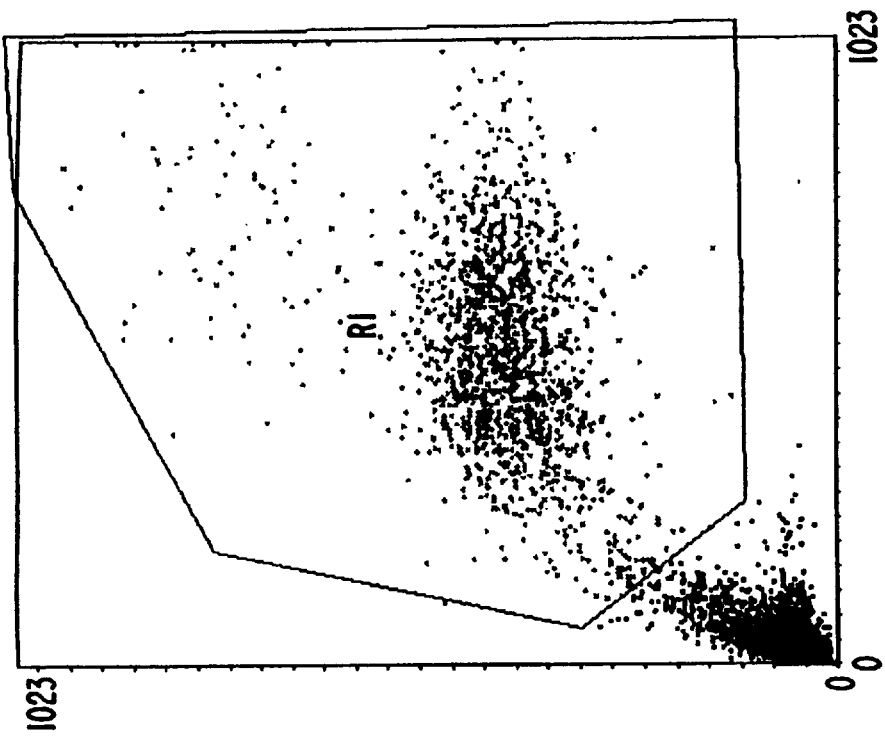
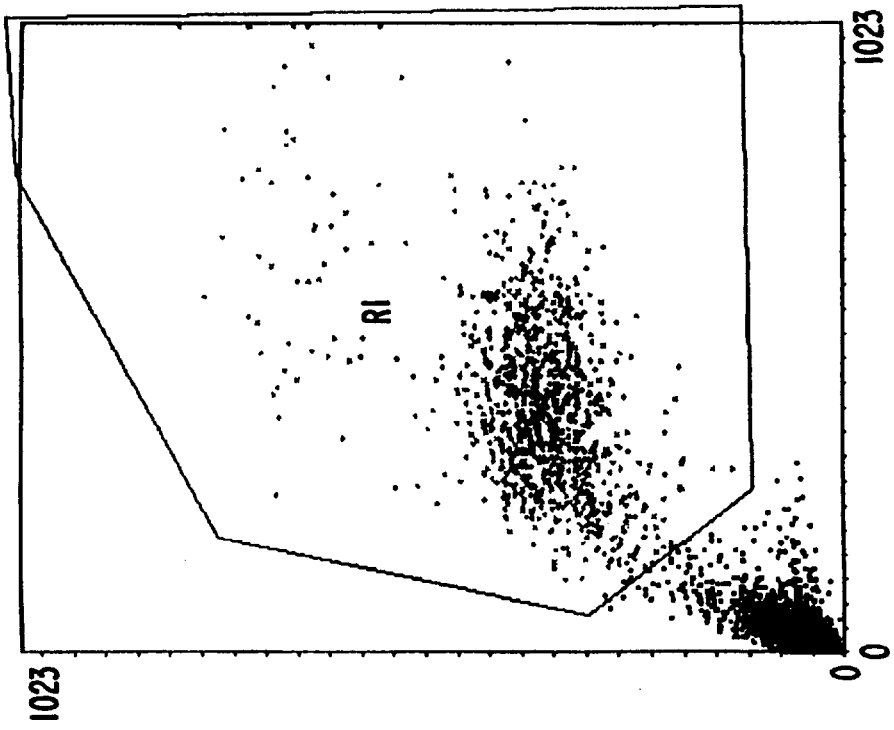

90° LS vs UMALS

90° LS vs UMALS

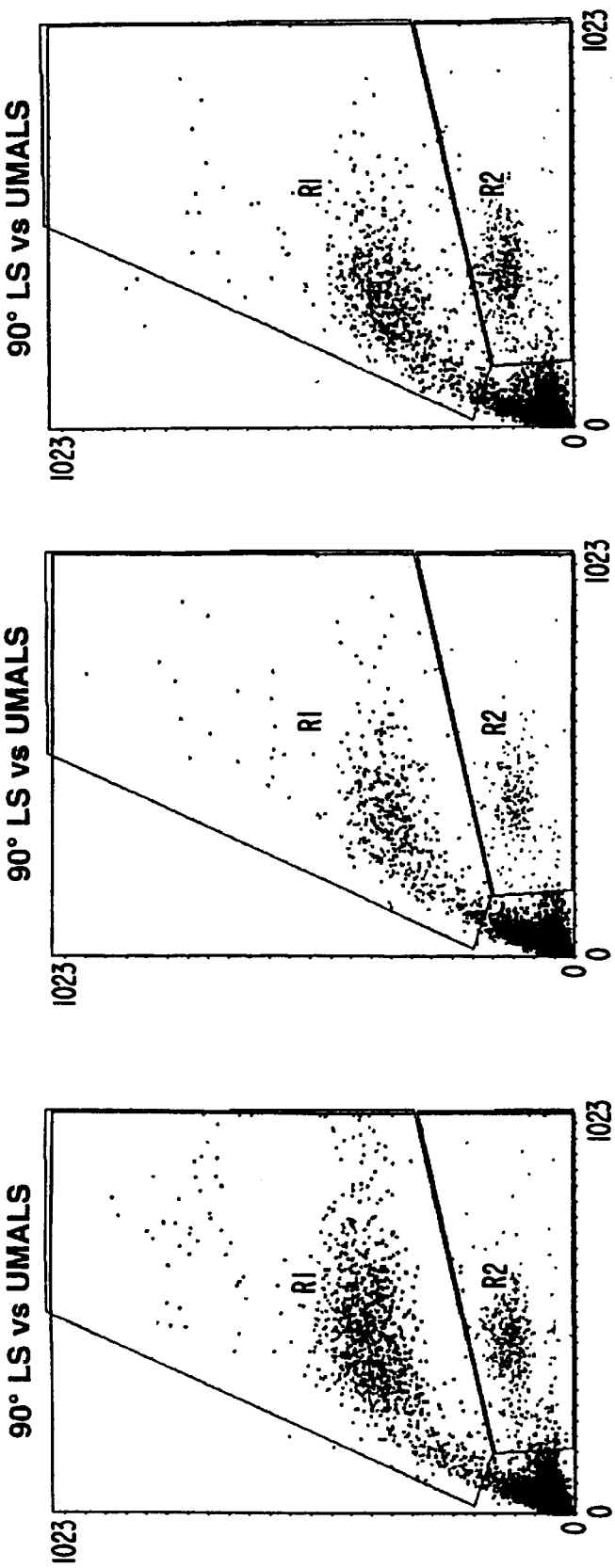

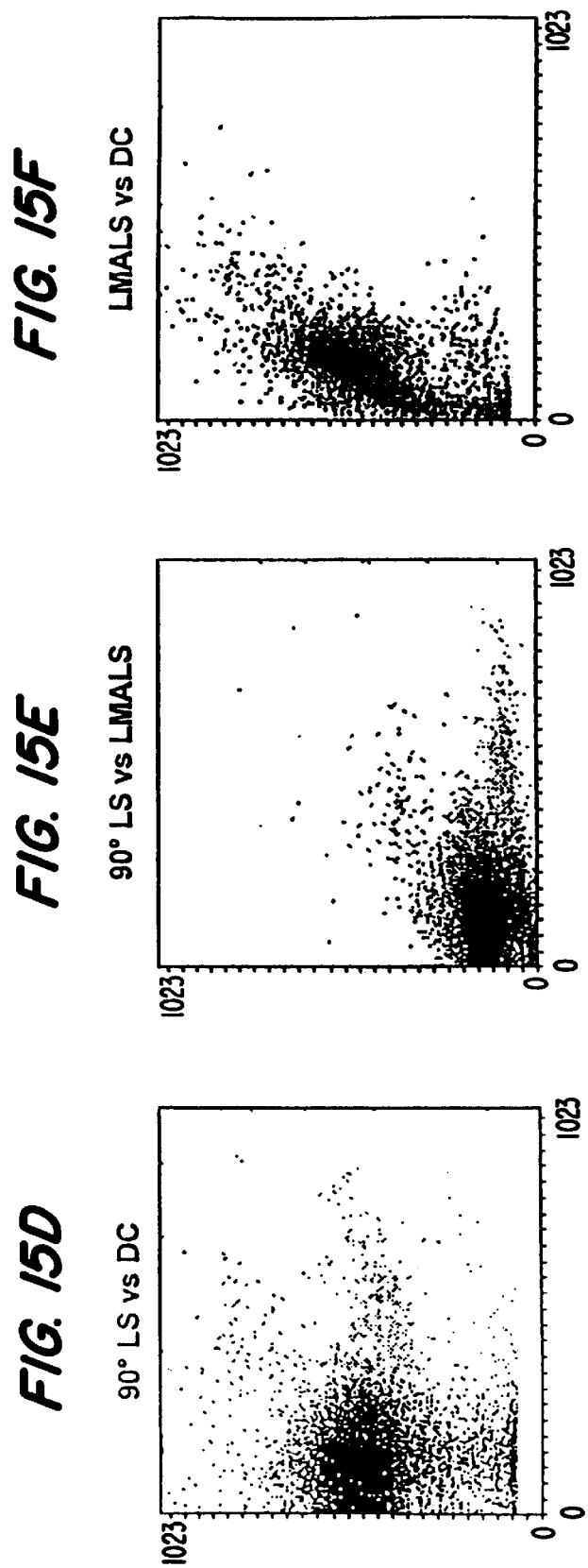

PROTEIN-COLLOIDAL METAL-AMINODEXTRAN COATED PARTICLE AND METHODS OF PREPARATION AND USE

FIELD OF THE INVENTION

This invention generally relates to novel flow cytometry, and cell separation, reagents, and more particularly to novel particles, in which a protein is conjugated to a colloidal-metal coated, aminodextran coated substrate and methods of preparation and use thereof.

BACKGROUND OF THE INVENTION

The technique of flow cytometry provides investigators with data on physical parameters of cells which can be used to separate various classes of cells, e.g., to classify white blood cells (leukocytes) into three major groups, namely, lymphocytes, monocytes and granulocytes. Other techniques have been described to identify additional leukocyte populations, for example, T-cells, B-cells, cytotoxic cells and suppressor cells, neutrophil, eosinophil, and basophils. See, e.g., *Flow Cytometry and Sorting*, page 371; edited by Melamed, Mullaney, and Mendelsohn, 1979, John Wiley & Sons, N.Y., N.Y.; U.S. Pat. No. 5,125,737; U.S. Pat. No. 5,492,833; U.S. Pat. No. 5,223,398; U.S. Pat. No. 5,231,005.

The enumeration of subclasses using antibody-coated polystyrene latex beads to target specific white blood cell subpopulations in whole blood, hence, producing a change (a shift) in the targeted cell volume, direct or low frequency current (DC) or high frequency (RF) conductivity, and light scatter (S) has been described. See, e.g., PCT Publication WO92/09682 published Jun. 11, 1992; J. C. Hudson et al, *Cytometry*, 22:150 (1995), U.S. Pat. No. 5,639,620 and International Patent application No. WO95/24631, published Sep. 14, 1995. In fact, these latter changes can be detected on the commercially available hematology instruments, such as the COULTER® STKS instrument equipped with VCS technology. Such instruments can calculate the percentage of shifted cell population in the total population of white blood cells.

All of the above bead-induced shift methods use a single type of polystyrene bead conjugated to an antibody to enumerate subpopulations of lymphocytes one at a time. The use of beads composed of inorganic materials to extend shifts has only recently been described. See, e.g., U.S. Pat. No. 5,466,609; International Patent Application No. WO9524631; and U.S. Pat. No. 5,552,086. Specifically, gold/silver colloid coated polystyrene-aminodextran beads, their preparation and characterization have been described. See, e.g., U.S. Pat. No. 5,248,772 and U.S. Pat. No. 5,552,086.

Current methods of obtaining lymphocyte differentials involve the use of fluorescence markers and measurement of forward light scatter, side light scatter and fluorescence intensity or the use of antibody on beads and measurement of median angle light scatter, DC, and RF. Heretofore, the use of antibody on beads has involved only a single type of bead coated with antibody at any one time to analyze for a single subpopulation of lymphocytes. See also, P. K. Horan and L. L. Wheeless, Jr., *Science*, 198:149–157 (1977); and British Patent No. 1561042, published Feb. 13, 1980. On the other hand, conventionally practiced flow cytometry with fluorescence markers simultaneously uses a number of fluorescent-labeled antibodies (2–6) to analyze for various subpopulations of leukocytes.

At present, there is no method that allows a sample of blood to be analyzed using the antibody on bead method, such that subpopulations of lymphocytes may be simultaneously enumerated. Thus, there exists a need in the art for compositions and methods which enable more efficient analysis of blood or other multicellular fluid materials.

SUMMARY OF THE INVENTION

In one aspect, the invention provides a stable colloidal particle comprising:
(a) a colloidal-sized core substrate having amine-reactive functional groups thereon;
(b) an aminodextran coating over the peripheral surface of said substrate;
(c) a layer of colloidal-sized metallic solid overlaying said aminodextran coating, wherein the metal for said metallic solid is selected from the group consisting of metals which can be reduced from the ionic state to the metal(O) state by the aminodextran coating of said core;
(d) a linker attached to said metallic solid, said linker having a free amino group; and
(e) a protein attached to said linker by covalently bonding to said free amino group.

In another aspect, the invention provides methods for preparing the above-described particles, including methods which employ an aminotrithiol linker, to enable the conjugation of protein to the coated particles.

In still another aspect, the invention provides methods for performing simultaneous quantitative determinations of two or more subpopulations of white blood cells in a biological solution or suspension, such as whole blood, using the above-described particles.

Other aspects and advantages of the present invention are described further in the following detailed description of the preferred embodiments thereof, reference being made to the accompanying figures.

BRIEF DESCRIPTION OF THE DRAWINGS

FIGS. 7A–7L illustrate matrices of pairs of parameters (DC v. LMALS; DC v. UMALS; LMALS v. PMT1; UMALS v. SALS; DC v. SALS, RF v. SALS, respectively) for mixtures of whole blood and T4-Amdex-Ag-Amdex-PS (7A–7F) or conventional T4-DAP-PS (7G–7L) particles, obtained with 633 nm excitation, showing the shifted location of targeted T4+ lymphocytes in each matrix.

FIGS. 8A–8L illustrate matrices of the same pairs of parameters as for FIGS. 7A–7L, for mixtures of whole blood and T4-Amdex-Ag-Amdex-PS or T4-DAP-PS particles, obtained with 780 nm excitation, showing the shifted location of targeted T4+ lymphocytes in each matrix.

FIGS. 9A–9F depict matrices of various pairs of parameters as indicated on the figures, for a mixture of whole blood and T4-DAP-PS particles, obtained with 633 nm excitation, showing the shifted location of T4+ lymphocytes.

FIGS. 10A–10F depict matrices of various pairs of parameters for a mixture of whole blood and T4-aminotrithiol-Au-Amdex-PS particles, obtained with 633 nm excitation, showing the shifted location of T4+ lymphocytes.

FIGS. 11A–11F depict matrices of various pairs of parameters for a mixture of whole blood and T4-Amdex-Ag-Amdex-PS particles, obtained with 633 nm excitation, showing the shifted location of T4+ lymphocytes.

FIGS. 12A–12D illustrate 90° LS versus UMALS matrices for mixtures of four samples of whole blood and T4-DAP-PS particles, obtained with 633 nm excitation, showing the shifted location, R1, of T4+ lymphocytes.

FIGS. 14A–14F show 90° LS versus UMALS matrices for mixtures of three samples of whole blood with, left-hand-side, T8-DAP-PS and T4-aminotrithiol-Au-Amdex-PS particle suspensions; and, right-hand-side, T4-DAP-PS and T8-aminotrithiol-Au-Amdex-PS particle suspensions, obtained with 633 nm excitation, showing the shifted locations of T8+(R1) and T4+(R2) lymphocytes on LHS and T4+(R1) and T8+(R2) lymphocytes on RHS.

FIGS. 15A–15F show matrices of various pairs of parameters for a mixture of whole blood with T4-DAP-PS and T8-Amdex-Ag-Amdex-PS particle suspensions, obtained with 633 nm excitation, showing the shifted locations of T4+(R1) and T8+(R2) lymphocytes.

DETAILED DESCRIPTION OF THE INVENTION

Figure 1:
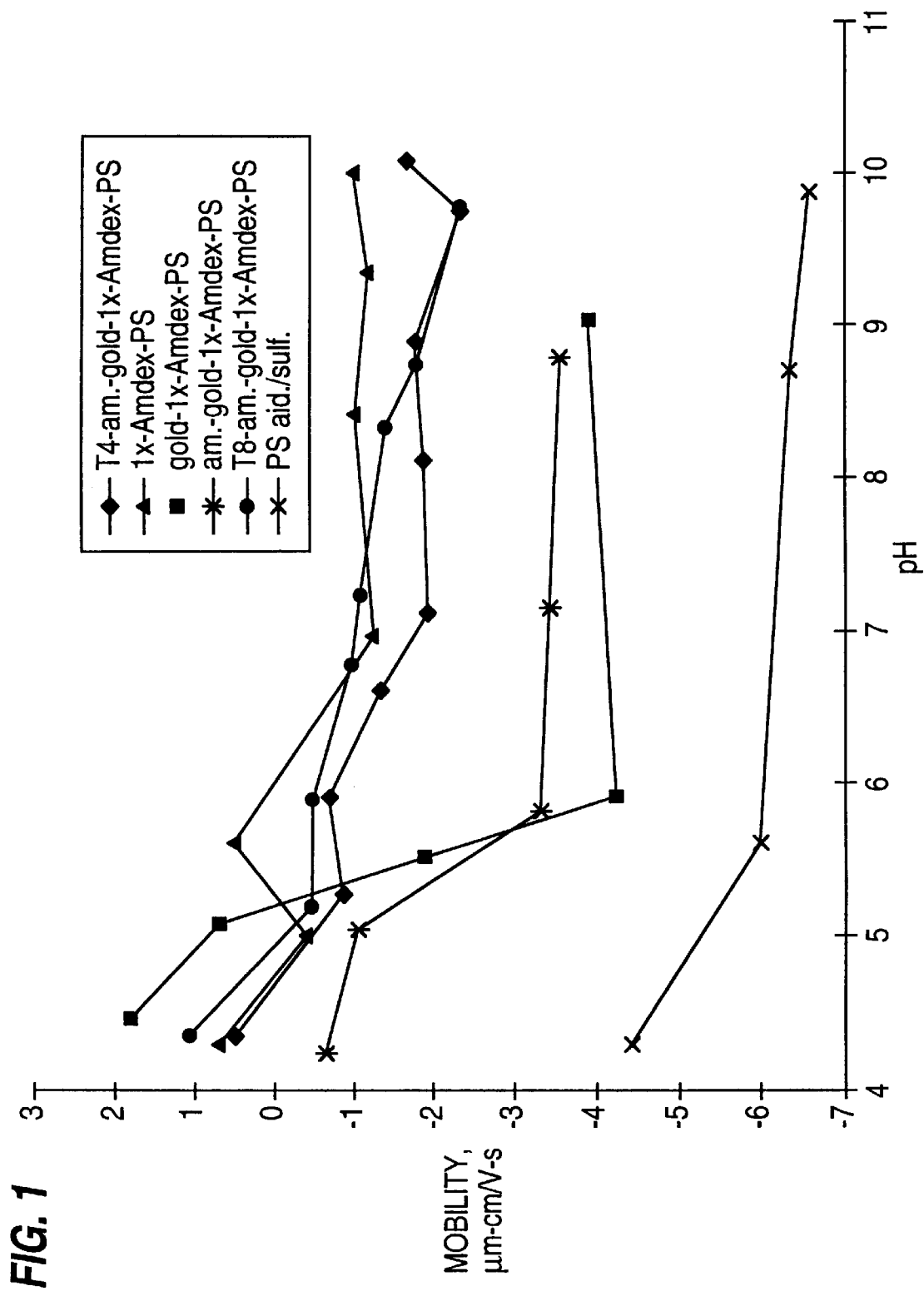
FIG. 1 is a graph plotting electrophoretic mobility versus pH data for suspensions of aldehyde/sulfate polystyrene latex beads (PS), uncoated or coated with aminodextran (Amdex), gold colloid, aminotrithiolate linker, and anti-CD4 (T4) antibody or anti-CD8 (T8) antibody.

The present invention meets the need in the art by providing novel stable colloidal particles, in which a protein, preferably an antibody, is conjugated to a colloidal-metal coated, aminodextran coated substrate. This particle may be employed in flow cytometry methods which permit the efficient analysis and separation of different cell types in a biological material, provided that each different cell type has at least one unique, non-overlapping antigenic epitope.

I. Definitions

The following terms as used herein and in the claims may be defined as follows.

A "histogram" is a graph of frequency distribution for a single variable, displayed as a two dimensional line graph with the variable plotted on the X axis and the frequency, designated as "number (#)", plotted on the Y axis. A histogram also is the abstract numerical tabulation of such a graph as represented within a computer or some other form of electrical circuit.

"Matrix" is a graph of frequency distribution for two independent variables, displayed as a three dimensional contour graph with one variable plotted on the X axis, the second variable plotted on the Y axis, and frequency or count displayed as iso-count contours. For clarity, only one iso-count contour is displayed to illustrate population outlines. Matrix also is defined as the abstract numerical tabulation of such a graph as represented within a computer or some other form of electrical circuit. When describing a matrix herein, the X axis variable is listed first, followed by the Y axis variable.

"Parameter" is synonymous with independent variable and refers to any of the simultaneous, independent measurements obtained from particles or cells being analyzed in a flow cytometer. The combination of two or more parameters, by some mathematical function, is defined as yielding another parameter.

"Gating" is a filtering process utilized in constructing, from multi-parameter data, a histogram of one parameter, while interrogating one or more of the other parameters. For each event, which is the passage of a single blood cell through the flow cell and the generation of cell measurements by the parameter transducers, the value or measurement corresponding to each parameter that is to be utilized for gating is compared with one or two reference values, or thresholds, and "tested" for being below the threshold, above the threshold, or between the two thresholds. If this test yields a true result for all the gating parameters being considered, then the event is included in the histogram. Gating also can be utilized to construct a matrix. Thus, by utilizing gating, it is possible to simplify the analysis and graphic representation of multi-parameter data.

"DC" and "RF" are electronic sensing parameters which refer to the Coulter Principle of aperture impedance cell sensing. "DC" is the pulse peak information obtained from applying a direct or low-frequency current, such that the cell membrane is not penetrated and no current flows through the cell. The peak amplitude of the DC pulse is a function of cell volume. "RF" is the pulse peak information derived from the measurement obtained by applying a high-frequency current, such that the cell membrane is short-circuited and current flows through the cell. RF is a function of cell volume and internal conductivity.

"LMALS" is Lower Median Angle Light Scatter, which is light received at the photodetector assembly scattered in or throughout the range of 10°–20° from the axis of the incident light beam.

"UMALS" is Upper Median Angle Light Scatter, which is light received at the photodetector assembly scattered in or throughout the range of 20°–65° from the axis of the incident light beam.

"SALS" or "90° LS" is Side Angle Light Scatter, which is light received at a photodetector assembly located in an approximate angular range of 90°+/±20° from the axis of the incident light beam.

The term "particle", also includes inter alia, microspheres, beads and spheres and such terms are interchangeable.

"Antibody" is defined to include polyclonal antibodies from any native source, and native or recombinant monoclonal antibodies of classes IgG, IgM, IgA, IgD, and IgE, hybrid derivatives, humanized or chimeric antibodies, and fragments of antibodies including Fab, Fab', and F(ab')$_2$.

II. Compositions of the Invention

The present invention provides a novel stable colloidal particle comprising:

(a) a colloidal-sized core substrate having amine-reactive functional groups thereon;

(b) an aminodextran coating over the peripheral surface of said substrate;

(c) a layer of colloidal-sized metallic solid overlaying said aminodextran coating, wherein the metal for said metallic solid is selected from the group consisting of metals which can be reduced from the ionic state to the metal(0) state by the aminodextran coating of said core;

(d) a linker attached to said metallic solid, said linker having a free amino group; and (e) a protein attached to said linker by covalently bonding to said free amino group.

In a preferred embodiment, the particles of the present invention comprise aminodextran coated polystyrene particles, which particles are also coated with a colloidal metal having a linking agent to which a crosslinker is attached. Protein, preferably antibody, is attached to the coated particles through the crosslinker to an amino group of the linker. These conjugates are particularly advantageous in that they enable the simultaneous analyses of at least two different subsets of white blood cells, for example, two subsets of T lymphocytes in a biological material containing white blood cells.

A. The Colloidal Metal-Aminodextran Coated Substrate

The coated substrate described above preferably has a core substrate (a) which is a polystyrene bead. Preferably the polystyrene bead ranges in size from between about 0.2 to about 5.0 microns in diameter (i.e., colloidal-sized). Such polystyrene core substrates containing aldehyde and/or sulfate functional groups are commercially available, e.g., from Interfacial Dynamics Corporation, Portland, Oreg. Of course, one of skill in the art may select other similar particles from other suppliers.

This core substrate has an aminodextran coating over its peripheral surface. Preferably the aminodextran coating (b) is covalently bonded to the core substrate (a) by covalent bonds between the free amino groups of the aminodextran and the amine-reactive functional groups of the polystyrene substrate and further by crosslinking with an agent such as glutaraldehyde. The aminodextran which forms coating (b) may generally be characterized as having a degree of diamine substitution in the range of 1/40–1/35 (1×-aminodextran) compared to a maximum theoretical value of 1/2.5. More preferably, the diamine substitution in the aminodextran coating (b) is approximately 1/7 to 1/8 (5×-aminodextran).

An alternative to this coated substrate employs carboxy functionalized polystrene particles as the core substrate, coated with aminodextran by EDAC coupling as described in U.S. Pat. No. 5,639,620.

The coated substrate also contains a layer of colloidal-sized metallic solid (c) overlaying this aminodextran coating. Preferably this layer is uniformly dispersed over the dispersed surface of the aminodextran layer. The colloidal metal useful in forming the coated substrate is generally described as a metal which can be reduced from the ionic state to the metal(0) state by the aminodextran coating, or a metal which can form metal ions or metal ion complexes which have a reduction potential of about +0.7 volts or higher. While such metal ions may include: Ag(I), Au(III), Pd(II), Pt(II), Rh(III), Ir(III), Ru(II), Os(II), the preferred metal ions for such use are colloidal gold(III) and colloidal silver(I).

B. The Linker

The present invention also provides for a linker which allows conjugation of a selected protein, e.g., an antibody, to the colloidal metal-aminodextran coated substrate described above. The linker generally has a free amino group which can be activated for conjugation to protein.

i. Aminodextran Linkers

One preferred linker which is introduced to overlay the colloidal metal-aminodextran coated substrate is an aminodextran linker, preferably an aminodextran in which the degree of diamine substitution is in the range of between about 1/40 and about 1/3 compared to a maximum theoretical value of 1/2.5, such as 1× aminodextran. Alternatively, the diamine substitution in the aminodextran linker may be between approximately 1/7 to 1/8, such as 5'-aminodextran. Preferably, the 5×-aminodextran linker is used where the colloidal metal is silver.

The aminodextrans contain sufficient amino groups to crosslink them to the existing particle surface of silver colloid-coated polystyrene particles as well as to covalently link them to a protein, e.g., antibody. The crosslinked aminodextran coating prevents the silver colloid from being shed from the polystyrene particles in subsequent chemical reactions needed to activate the particles, conjugate them to monoclonal antibody, and block chemically-reactive functional groups.

ii. Aminotrithiol Linker

Another preferred linker, particularly useful where the colloidal metal is gold, is an aminotrithiolate linker. A particularly useful aminotrithiol linker is tris(3-mercaptopropyl)-N-glycylaminomethane, a spider-like composition having the formula, $C_{12}H_{26}N_2OS_3$, [J. K. Whitesell and H. K. Chang, Science, 261: 73–76 (1993)] and the structural formula:

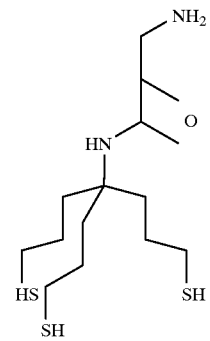

This compound was originally described as forming a layer on a roughened gold film surface, to provide $NH_2$ initiation sites for polymerization of alanine N-carboxyanhydride to form polyalanine helices that uniformly aligned themselves perpendicular to the surface. The polyalanine helices were shown to remain attached to the gold surface and retain their conformation even after heating to 180° C. for one week.

The preferred form of this linker is the freshly deprotected form, which is preferably prepared as described in detail in Example 4A below. Example 4 demonstrates that the aminotrithiol linker functions well as a ligand between gold particles deposited on polystyrene particles and monoclonal antibodies. By coordinating strongly to gold or silver atoms on colloidal metal through its three sulfur atoms, and allowing activation and conjugation of antibody through its amino group, the aminotrithiol linker also serves as a new bifunctional linking agent. The soft base, highly polarizable sulfur atoms of low electronegativity prefer to coordinate to the soft acid, gold or silver atoms.

However, as discussed in Example 5B below, the aminotrithiol linker competes too well with aminodextran for binding sites on the surface of deposited silver colloid on polystyrene particles and displaces much of the silver colloid from the surface of silver-aminodextran-polystyrene particles. Thus, aminotrithiol does not work well as a crosslinking agent with silver colloid on polystyrene particles.

C. The Cross-Linking Agent

The linker as described above is covalently bonded to the colloidal metal-aminodextran-coated substrate or the aminodextran-metal-aminodextran-coated substrate. For activation of the linker on the particles, a heterobifunctional cross-linking agent, such as sulfosuccinimidyl 4-[N-maleimidomethyl]cyclohexane-1-carboxylate ("sulfo-SMCC") is used. Sulfo-SMCC covalently bonds to a linker with reactive amino groups. Various other suitable crosslinking agents and methods are cited in texts such as The Pierce Handbook and *Chemistry Of Protein Conjugation And Cross-Linking,* S. S. Wong, CRC Press, Inc., Boca Raton, Fla. (1991).

D. The Protein

The selected activated protein, then attached through the crosslinker to the linking agent on the colloidal metal-aminodextran coated substrate to form the novel, stable colloidal particle of the invention, is preferably an antibody. More specifically, the protein (e) is covalently bonded to the linker-colloidal metal-aminodextran coated substrate by covalent bonding of the free amino groups on the linker through the heterobifunctional crosslinker with sulfhydryl or amino groups on the activated protein.

Although any protein may be attached to the substrate in this way, preferably, the protein is a monoclonal or polyclonal antibody or any one of a variety of recombinant antibody constructs. The antibody is desirably directed to an epitope on a cell, which epitope is unique to the cell type, thereby permitting the particle's use in cell separation assays. Polyclonal antibodies may be generated by conventional means, i.e., obtained from sera of animals or humans exposed to a selected antigen. For example, polyclonal antibodies are generated by conventionally stimulating the immune system of a selected animal or human with a selected antigen, allowing the immune system to produce natural antibodies thereto, and collecting these antibodies from the animal or human's blood or other biological fluid.

Monoclonal antibodies are obtained by conventional hybridoma methods and purified from ascites fluid by ammonium sulfate (45%) precipitation, centrifugation and affinity chromatography using protein A. Processes of making monoclonal antibodies are described in G. Kohler and C. Milstein, *Nature,* 256:495–497 (1975) and include the many known modifications thereof, which teachings are incorporated herein by reference. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science,* 233:747–753 (1986); Queen et al., *Proc. Nat'l. Acad. Sci. USA,* 86:10029–10033 (1989); PCT Patent Application No. PCT/WO9007861; and Riechmann et al., *Nature,* 332:323–327 (1988); Huse et al, *Science,* 246:1275–1281 (1988)a].

One of skill in the art may generate chimeric, humanized or fully human antibodies for use as the protein of this invention by resort to known techniques by manipulating the complementarity determining regions of animals or human antibodies. See, e.g., E. Mark and Padlin, "Humanization of Monoclonal Antibodies", Chapter 4, *The Handbook of Experimental Pharmacology,* Vol. 113, The Pharmacology of Monoclonal Antibodies, Springer-Verlag (June, 1994).

Of course, the particular method of making and the type of antibody is not limited to such techniques and it is envisioned that any technique for making such antibodies is within the practice of the invention. In a preferred embodiment, the protein is a monoclonal antibody to the CD3, CD4 or CD8 receptors on T lymphocytes. Examples of such monoclonal antibodies are the following: monoclonal antibody (MAb) "T3" (commercially available from Coulter Corporation, Miami, Fla.) is an anti-CD3 antibody of IgG1 subclass, derived from the hybridization of mouse P3/NS1/1-AG4-1 myeloma cells with spleen cells from BALB/c mice immunized with human infant thymocytes and peripheral blood lymphocytes from a patient with Sezary cell leukemia.

MAb "T4" (Coulter Corporation) is an anti-CD4 antibody derived from hybridization of mouse NS/1-AG4 cells with spleen cells of BALB/cJ mice immunized with human peripheral blood T lymphocytes. MAb "T8" is an anti-CD8 antibody, derived as described for T4, but immunized with human thymocytes (Coulter Corporation). MAbs T4 and T8 are chosen for use in the examples below for the large density of their antigenic receptors ($10^4$–$10^5$ receptors per targeted cell) and the mutual exclusiveness of their targeted cells.

However, as the protein portion of the novel particle, any antibody directed against any targeting receptor site on a cell may be used, as long as the sites per cell are greater than about $10^3$ and each such site is exclusive to one cell population in multiple targeted cell populations.

E. Embodiments of Particles of the Invention

An exemplary embodiment of the stable particle of this invention is the particle comprised of colloidal-sized polystyrene microparticle having a 1×-aminodextran coating over the peripheral surface thereof, and a layer of colloidal-sized gold overlaying the aminodextran coating. An aminotrithiolate linker having a free amino group is covalently bound to the gold, and an anti-CD4 antibody is attached to the linker via a heterobifunctional crosslinker. This particle is referred to as the T4-aminotrithiolate-gold-1×-aminodextran-polystyrene particle.

Another exemplary particle is made up of a colloidal-sized polystyrene particle having a 1×-aminodextran coating over the peripheral surface thereof, with a layer of colloidal-sized silver overlaying the aminodextran coating. A 5×-aminodextran linker having free amino groups is cross-linked around the silver-aminodextran-PS particle, and an anti-CD4 antibody is attached to said linker by covalently bonding to the free amino group through a heterobifunctional crosslinker, such as sulfo-SMCC. This particle is referred to as the T4-5×-aminodextran-silver-1×-aminodextran-polystyrene particle.

Another embodiment of a particle according to the invention comprises a colloidal-sized polystyrene particle with a 1×-aminodextran coating over the peripheral surface thereof, with a layer of colloidal-sized gold overlaying the aminodextran coating. An aminotrithiolate linker having a free amino group is crosslinked to the gold and an anti-CD8 antibody protein is attached to the free amino group of the linker via a heterobifunctional crosslinker. This particle is referred to as the T8-aminotrithiolate-gold-1×-aminodextran-polystyrene particle.

Yet another embodiment of a particle according to this invention comprises a colloidal-sized polystyrene particle having a 1×-aminodextran coating over the peripheral surface thereof, with a layer of colloidal-sized silver overlaying the aminodextran coating. A 5×-aminodextran linker having free amino groups is cross-linked around silver-aminodextran PS particle and an anti-CD8 antibody is attached to said linker by covalent bonding to the free amino groups through a heterobifunctional crosslinker, such as sulfo-SMCC. This particle is referred to as the T8-5×-aminodextran-silver-1×-aminodextran-polystyrene particle.

These exemplary stable particles of the present invention are particularly desirable as reagents for use in a method of simultaneously analyzing a biological fluid, such as whole blood, for at least two different, mutually exclusive subsets of lymphocytes.

III. Methods of Preparing the Particles of the Invention

The present invention further provides methods for the preparation of the novel stable colloidal particles described herein. Generally, the particles of the invention are prepared by reacting aminodextran coated polystyrene particles with metal salts, attaching a linker thereto and attaching a protein, e.g., an antibody, to the coated particle through the linker.

More specifically, the method for preparing such particles, comprises the first step of reacting commercially available aldehyde functionalized polystyrene particles with aminodextran as described above. Some aminodextran adsorbs onto the surface of, and covalently binds to, a colloidal-sized polystyrene core substrate. Additional aminodextran is covalently bound to the beads by crosslinking with glutaraldehyde. The resulting reaction mixture is treated with a reducing agent to obtain stable, coated beads. This reducing agent can be any conventional reducing agent, such as sodium borohydride. The resulting cross-linked aminodextran coated polystyrene particles are subsequently washed with water, preferably distilled water. The aminodextran is generally capable of reducing a metal ion or metal ion complex to the metal(0) state, i.e., reducing gold(III) to gold(0) or silver(I) to silver(0).

These aminodextran-coated polystyrene particles are then reacted with an aqueous solution of a metal salt, containing an metal ion or metal ion complex which is capable of being reduced by the aminodextran coating. As discussed above, the metal salt is preferably a gold(III) or silver(I) salt. Briefly described, the aqueous suspension of the coated particles is mixed with an excess of aqueous solution of the metal salt at an elevated temperature, in the presence of a predetermined amount of a second reducing agent which reduces the excess metal ion to the metal(0) state, mainly as colloidal metal on the surface of polystyrene particles. The elevated temperature ranges desirably between about 80 to about 100° C. The additional reducing agent is sodium citrate, which is used for rapid formation of colloidal metal.

The resulting colloidal metal-aminodextran coated particles are purified by washing, for example, with aqueous sodium citrate solution and distilled water.

Further steps involved in preparing the novel particles of the present invention include attaching a linker or linking agent having a free amino group to the colloidal metal-aminodextran coated particles. The linker allows conjugation of proteins to the surface of the metal-colloid coated particles. Preferably, for silver-coated particles or beads the linker is aminodextran, and most preferably 5×-aminodextran. For gold-coated beads the linker is preferably the aminotrithiolate linker described above.

Where the linking agent is an aminodextran, it may be attached to the coated particles by adsorption and crosslinking with a bifunctional crosslinking agent, such as glutaraldehyde. The free amino groups on the aminodextran linker are then activated with a suitable heterobifunctional crosslinking agent which links the colloidal metal particle to the protein, for example, sulfosuccinimidyl 4-[N-maleimidomethyl]cyclohexane-1-carboxylate (sulfo-SMCC) or others known to the art as described above.

The aminotrithiol linker may be attached by reaction of thiolate groups with the colloidal gold-surface. More specifically, the method of using the aminotrithiol linker comprises dissolving protected aminotrithiol ligand in anhydrous methanol; adding concentrated hydrochloric acid to the resulting solution; and refluxing the mixture. In one embodiment a preferred time for refluxing is about 5 hours. The components of the mixture are separated, e.g., by size exclusion chromatography on a BioGel P2® gel, and fractions of the first band (representing deprotected aminotrithiol ligand) absorbing at 280 nm, are collected. The deprotected aminotrithiol ligand is then mixed with the gold colloid-aminodextran-coated polystyrene beads described above. Thus strong covalent bonds are formed between the sulfur groups on the linker with the gold colloid surface. The free amino group of the linker is then activated with sulfo-SMCC.

Once the crosslinker is attached to the particle, a selected protein which is desired to be attached to the colloidal particle is then conjugated to the amino groups of the activated linker on the coated particles by conventional methods, e.g., by activating the protein with an amino binding reagent which provides a sulfhydryl group. A suitable amino binding/activating reagent is 2-iminothiolane. Conventional methods of 2-iminothiolane activation of antibody and maleimide (sulfo-SMCC) activation of amino groups on coated particles to conjugate antibody to particles, are described in *Chemistry Of Protein Conjugation And Cross-Linking*, S. S. Wong, CRC Press, Inc., Boca Raton, Fla., 1991. Still other amino-reactive sulfhydryl introducing reagents may readily be selected by one of skill in the art from available texts [See, also, Pierce Handbook].

Finally, the activated colloidal metal-coated, linker coated particle is purified and the activated protein is purified, both by conventional means. The purified particles in aqueous suspension are then mixed with an amount of an aqueous solution of the activated protein sufficient to saturate the reactive groups on the activated particles. This mixing preferably occurs at room temperature and for a time sufficient to permit conjugation between the protein and particle, resulting in a stable colloidal particle. Selection of the amount of the activated protein solution and the mixing times are clearly within the skill of the art, depending upon the amount of particle to be conjugated to protein, and these parameters are limitations of this method.

Preferably, before use, unreacted functional groups on the resulting stable colloidal particles are blocked with appropriate blocking agents, such as L-cysteine and iodoacetamide. For use in biological assays, exemplary particles of the invention, e.g., antibody-conjugated gold- or silver-coated polystyrene particles, may be suspended in suitable buffers, such as bovine serum albumin (BSA) buffer.

IV. Methods of Use—Simultaneous Analysis

The above-described colloidal particles of this invention are desirably employed in methods of simultaneous quantitative determination of at least two different subsets of cells. For example, one exemplary method employing the particles of the invention demonstrates the simultaneous quantitative determination of two or more subpopulations of white blood cells in a biological solution/suspension containing both red blood cells and white blood cells. Preferably, the subsets of cells are characterized as having some antigenic site which is mutually exclusive and non-overlapping.

Thus, a method of the present invention comprises the steps of mixing a biological solution or suspension, e.g., whole blood, with at least two different stable colloidal particles as described above. Each different particle contains a different protein, e.g., a different antibody, conjugated thereto and each protein binds to a different epitope on a subpopulation of white blood cells. The particles and biological material are mixed for a time sufficient to permit the binding of the particles to each subpopulation of cells.

Thereafter, the red blood cells in said biological solution/suspension are lysed and quenched. This mixture is analyzed in an instrument that distinguishes between the subpopulations of white blood cells bound by each different colloidal particle, thereby quantitatively enumerating at least two subpopulations of the white blood cells. Preferably, the instrument analyzes the mixture simultaneously and distinguishes between cells by shifting light scatter of targeted cells in VCS (i.e., volume, conductivity and light scatter) technology. In a preferred embodiment, the detection instrument is equipped with at least two lasers. One particularly desirable instrument for such use is a modified Coulter VCS instrument which is described in U.S. Pat. Nos. 5,125,737 and 5,492,833, incorporated herein by reference.

By such a method, one may quantitatively detect subpopulations of white blood cells, such as $CD^{4+}$ T lymphocytes ("T4 cells"), $CD8^+$ T lymphocytes ("T8 cells"), B lymphocytes, granulocytes, basophils, and monocytes, among others.

As illustrated in Example 8 below, the method of the present invention further provides for the simultaneous analysis of T4 and T8 cell populations in whole blood using three different colloidal particles. One particle was a commercially available polystyrene bead, the other particles were particles of the invention, i.e., the T4-aminotrithiolate-gold-1x-aminodextran-polystyrene particle and the T8-5x-aminodextran-silver-1x-aminodextran-polystyrene particle.

The following examples are provided to illustrate the invention. Specifically, Examples 1–4 illustrate the preparation of particles of the invention. Example 5 provides analytical evaluation of the particles. Examples 6 and 7 provide separate analyses of cell populations, and Example 8 provides an example of simultaneous analysis of cells using the present invention. These examples are illustrative only and do not limit the scope of the invention. Further, one skilled in the art will appreciate that although specific reagents and conditions are outlined in the following examples, modifications can be made which are meant to be encompassed by the spirit and scope of the invention.

Example 1—Coating of Polystyrene Aldehyde/Sulfate Particles with 1x-Aminodextran or 5x-Aminodextran A. Polystyrene Microspheres Raw polystyrene aldehyde/sulfate latex particles were obtained from Interfacial Dynamics Corporation (IDC), Portland, Oreg. Initial studies of T4-5x-Amdex-PS and T4-Ag-5x-Amdex-PS particles were carried out with IDC lot 2-300-36 particles of mean diameter 2.15 μm, CV=5.5% as measured by transmission electron microscopy (TEM). IDC lot 496 particles, which were reported to have a mean diameter of 2.200 μm, CV 5.4% as determined by TEM and found to have a mean diameter of 2.021 μm, CV=1.0% as measured by quasi-elastic light scattering (QELS) on the COULTER® N4MD sub-micron particle analyzer, were later used in preparing T4, T8-PS particles. All later gold or silver-coated PS particles were prepared from IDC lot 540 particles, which had a mean diameter of 2.130 μm, CV=2.7% by TEM and of 2.007 μm, CV=1.1% by QELS.

B. Coating with Aminodextran

These colloidal particles were prepared in a manner substantially as described in U.S. Pat. No. 5,639,620, incorporated by reference. Briefly, 36.6 mL of 4.1% w/v solids of these particles were pipetted into a 250 mL polypropylene centrifuge tube. These particles were coated with aminodextran as follows. To the above-described suspension was added 3.0 g of 1x- or 5x-aminodextran, dissolved in 50 mL hot, distilled water and filtered through a 250 mL 0.2 μm filter pack. The 1x or 5x-aminodextran was prepared by the procedures described in U.S. Pat. No. 5,466,609. Distilled water was then added to the mixture to make a total volume of 150 mL, and 18.3 μL of 45% w/w potassium hydroxide solution was added to make the mixture 1 mM in potassium hydroxide. The tube and contents were roller mixed for 16 to 24 hours.

C. Crosslinking

Crosslinking of the aminodextran was accomplished with 3 mg/mL or 1.8 mL of 25% glutaraldehyde, reacted with the particle suspension for one hour. A light yellow color in the particle mixture was noted at the end of the mixing period. Sodium borohydride solid at 10 mg/mL or 1.531 g was added to the reaction tube, which was then roller mixed for an additional three hours. An extra 1.834 mL of 45% w/w potassium hydroxide solution was also added to the tube to reduce the evolution of hydrogen gas. The yellow color of the reaction mixture, due to the Schiffs' base generated in the reaction with glutaraldehyde, changed to a colorless, white particle suspension after about 15 minutes of mixing with sodium borohydride. Gas was released 2–3 times over the three hour mixing period.

The particles were then separated by centrifugation for about 15 minutes at 3400 g in a Beckman J6-B centrifuge, the clear supernatant was discarded, and the residue was washed four times with 150 mL distilled water. The residue was resuspended each time by vigorously vortexing and sonicating for 2 to 5 minutes to redisperse the particles.

The resulting aminodextran coated polystyrene particles are referred to as 1x-Amdex-PS and 5x-Amdex-PS.

Example 2—Coating of the 1x-Amdex-PS and 5x-Amdex-PS Microspheres with Colloidal Metal A. Coating of Particles with Silver The particles of Example 1 were coated with silver colloid substantially as described in U.S. Pat. No. 5,552,086. Briefly, 3.12 mL of 0.589 M silver nitrate solution was added to 540 mL of distilled water in a 1 L, 3-neck, round bottom flask. The solution was stirred with an overhead glass rod sleeve stirrer and heated to about 90° C. with a heating mantle (Glas-Col), top and bottom. 30 mL of 1% w/v solids 1x-Amdex-PS of Example 1 were added to the colorless, hot silver nitrate solution and the resulting mixture was stirred, with heating, for about 1 to 2 minutes. 48 mL of 1.36 M sodium citrate solution was then added to the hot, stirred reaction mixture.

Reaction progress to form colloidal silver on the particles was noted at various times from the color of the suspension: about 2 minutes; pale yellow; about 4 minutes, dark brown; about 7 minutes, black; about 10 minutes, dark grey; about 15 minutes, dark grey. After 15 minutes, the reaction was quenched by pouring the contents of the flask into a 1 L beaker and allowing the particle suspension to cool to room temperature. The dark grey particles settled after about 40 minutes, at which time the supernatant was decanted and the residue of about 50 mL was resuspended in 0.01 M sodium citrate solution to 100 ml total volume. The particles were separated and washed by centrifugation for about 5 minutes at 500 g, and finally dispersed in 0.01 M sodium citrate solution at a total volume of 30 mL.

B. Scale Up Preparation

Five times scale-up preparation is similar to that described in Part A above, however, 15.6 mL of 0.589 M silver nitrate solution in 2600 mL distilled water, 150 mL of 1% w/v solids 1x- or 5x-aminodextran-polystyrene particles, and 240 mL of 1.36 M sodium citrate solution are needed. About a 15 minute reaction time and about 90° C. reaction temperature were still used for reactants in a 5 L, 3-neck, round bottom flask with overhead stirring and top and bottom heating mantles. At the end of the reaction period the 5 L flask and contents were removed from the mantles and cooled for about 10 minutes, upon which all particles had settled to the bottom of the flask as a black solid. Almost all the supernatant was then discarded by decantation, leaving a dark grey suspension of particles which were resuspended to a total volume of 125 mL with 0.01 M sodium citrate solution.

The particles were separated and washed two times with 0.01 M sodium citrate solution by centrifugation for about 5 minutes at 500 g, and finally redispersed to a total volume of 150 mL with 0.01 M sodium citrate solution.

C. Analysis of Silver-1x-Amdex-PS and Silver-5x-Amdex-PS Particles

Microscopic examination at 1000x magnification of 10 times diluted particles of Part A in 0.01 M sodium citrate solution showed mostly single primary particles and small aggregates (2–3 primary particles) with very few large aggregates. The relative populations of singlets (single, primary particles), doublets (two primary particles stuck together), higher order multiplets (three or more primary particles stuck together), and uncoated or lightly-coated PS particles in a colloidal suspension of the metal-coated 1x-Amdex-PS and metal-coated 5x-Amdex-PS particles were measured on a flow cytometer (COULTER Profile II with 488 nm Ar ion laser excitation for silver-Amdex-PS particles; and COULTER Elite with 633 nm He/Ne laser excitation for both gold- and silver-Amdex-PS particles).

The populations of these primary and aggregated particles with different sizes and shape are well-defined in their light scattering ability if the primary particles are monodisperse and the gold or silver coatings are uniform. Serial dilutions of particle concentrates were made with twice-filtered 1 mM potassium hydroxide solution so that the volume fraction of particles in the final suspension was about $1.3 \times 10^{-5}$. The flow cytometer was optically aligned with DNA-Check particles to give HPCV 2.0% for FS and SS, and F11 and F12 parameters in histograms and calibrated with Standard-Brite particles.

Operating parameters were selected as follows: sample aspiration volume of 50 µL; sample flow rate of 10 L/min so that total sample running time will coincide with 10,000 events; histogram parameter Y-axis as FS and X-axis as SS; amplifier gain for FS in the middle of the linear gain versus mean channel (Y-axis) region; PMT voltage for SS in the middle of the linear voltage versus mean channel (X-axis) region; histogram 1 (entire region) and 2 (gated on bitmap 1) as 64×64 type, FS-SS, with bitmap 1 encompassing single particles in box 1, doublets in box 2, and all higher order aggregates in box 3, but leaving out amplifier noise; appropriate scaling factor for histograms 1 and 2; bitmap 1 and histogram 2 to count 10,000 events; histogram 2, gated on bitmap 1, and set up analysis boxes, 1 for single particles, 2 for doublets, and 3 for multiplets in the same position as in histogram 1. The percent population of each particulate state was read from the extended printout of histogram 2. The analysis boxes on histogram 1 do not reflect the true percentage ratios of particles, since they include electronic noise and any small particles outside of bitmap 1 in histogram 1.

Flow cytometry (forward versus side scatter) histograms gave 65% singlets, 32% multiplets, and 3% uncoated polystyrene particles.

Microscopic examination of a 10-fold diluted suspension of the scaled up preparations of Part B showed mostly black singlets, many doublets, and some larger clusters. All polystyrene particles of two micron nominal diameter were evenly and densely-coated with black silver particles of diameters ranging from 50 to 200 nm. Flow cytometry showed 74% singlets, 22% multiplets, and 4% uncoated polystyrene particles, and a mean shift of silver-polystyrene particles with 488 nm laser excitation of 40.1 (3.3) on the side scatter axis compared to polystyrene particles of 15.5 (1.6).

D. Coating of Particles with Gold

The preparation of colloidal gold coated 1x-Amdex-PS and 5x-Amdex-PS particles of Example 1 was performed substantially as described in U.S. Pat. No. 5,552,086. Briefly, 0.740 g of hydrogentetrachloroaurate(III), $HAuCl_4 \cdot 3H_2O$, were dissolved in 270 mL distilled water in a 1 L, 3-neck, round bottom flask and heated to about 80° C. with top and bottom heating mantles, and overhead stirring. 30 mL of 1% w/v solids 1x- or 5x-aminodextran-polystyrene particles of Example 1 were added to the hot, stirred solution and allowed to mix for about 5 minutes. 1.5 mL of 1.36 M sodium citrate solution was then pipetted into the stirred, hot mixture.

Within 5 seconds the color of the reaction mixture turned from pale yellow to colorless and in about 25 seconds, turned to brown. After one minute of reaction, heating and stirring were stopped and the contents of the flask were transferred to a 1 L beaker, wherein the particle suspension was sonicated for about 1–2 minutes and allowed to cool to room temperature. Then, the brown particles were separated by centrifugation for about 5 minutes at 500 g, the supernatant was discarded, and the residue was washed two times with 0.01 M sodium citrate solution and resuspended finally to a total volume of 30 mL with 0.01 M sodium citrate solution.

E. Scale Up Preparation

The 5-fold scale-up preparation was similar to that of Part B; however, 3.58 g of hydrogentetrachloroaurate(III) in 2800 mL of distilled water and 150 mL of 1% w/v solids 1x- or 5x-aminodextran-polystyrene particles were mixed at about 80° C. for 56 minutes in a 5 L, 3-neck, round bottom flask, with overhead stirring and top and bottom heating mantles. Then, 7.5 mL of 1.36 M sodium citrate solution were added to the mixture. In 10 seconds the reaction mixture turned from pale yellow to colorless, then, in 30 seconds, to purple, and in 55 seconds, turned to brown. The reaction was continued at about 80° C. for about another 9 minutes. At the end of the reaction period, heating and stirring were stopped and the 5 L flask and contents were removed from the mantles and allowed to cool to room temperature. After about one hour, the light purple supernatant was decanted and a heavy brown suspension of about 150 mL was separated by centrifugation for 5 minutes at 500 g. The supernatant was discarded, and the residue was washed two times with 0.01 M sodium citrate solution and finally resuspended in 0.01 M sodium citrate solution to a total volume of 150 mL.

The amount of gold salt that was used per milliliter of 1% w/v particles was chosen so that the volume of metallic gold that could be formed was equivalent to the volume of metallic silver that could be formed in Part B assuming 100% reduction of each metal ion to metal (0). In the large scale silver coating procedure of Part B, the volume of silver metal that could be formed is 15.6 mL/(1000 mL/L)×0.589 M $AgNO_3$×107.87 g Ag/mol÷10.49 $g/cm^3$=0.0945 $cm^3$ Ag. Thus, the mass of gold salt, $HAuCl_4.3H_2O$, that is required in the large scale gold coating procedure is 0.0945 $cm^3$ Au×19.32 $g/cm^3$×393.88 g $HAuCl_4.3H_2O$/196.97 g Au=3.65 g per 150 mL of 1% w/v particles. The volume fraction in silver or gold coated on polystyrene particles, 0.05% w/v solids, was $3×10^{-6}$ in the reaction mixtures, but was concentrated to $6×10^{-5}$ in the final suspension of polystyrene particles. The added metal changes the original 1% w/v solids particle suspensions to about 2.2% w/v solids gold-Amdex-PS particles and to about 1.7% w/v solids silver-Amdex-PS particles, as measured by washing an aliquot of particle suspension exhaustively, 5 or 6 times, with distilled water, freeze-drying the washed sample, and weighing the sample.

F. Analysis of Gold-1x-Amdex-PS and Gold-5x-Amdex-PS Particles

Microscopic examination of 10-fold diluted particles of Part D showed singlets, small aggregates, and very few large aggregates. Flow cytometry (forward versus side scatter) histograms performed as described above for the silver coated particles showed a mean shift of gold-polystyrene particles with 633 nm laser excitation of 42.0 (4.7) on the side scatter axis compared to polystyrene particles of 16.0 (2.5). The percentage of gold-Amdex-polystyrene singlets was 43%, aggregates, 53%, and uncoated polystyrene particles, 4%.

Flow cytometry performed on the scaled up preparation of Part E showed that the percentage of singlets was 53%; multiplets, 26%; and lightly-coated polystyrene particles, 16%.

Example 3—Crosslinking and Conjugation of the Colloidal Silver-Aminodextran-Polystyrene Particles A. Preparation of 5x-Aminodextran Cross-Linked Silver-Amdex-PS Particles 25 mL of silver-aminodextran-polystyrene particles prepared from 1% w/v solids polystyrene particles and suspended in 0.01 M sodium citrate solution as described in Example 2A were separated by centrifugation for 5 minutes at 500 g, the supernatant was discarded, and the residue was resuspended in a 2% w/v 5x-aminodextran solution at the original volume. The mixture was roller mixed overnight for 16–24 hours, centrifuged for about 5 minutes at 500 g to separate the residue and discard the supernatant. The final residue was resuspended to a total volume of 25 mL with 1 mM potassium hydroxide solution.

Thereafter, 0.10 mL of 25% w/v glutaraldehyde was added to the particle suspension to make a 1 mg glutaraldehyde/mL particle suspension, which was roller mixed for about 50 minutes. Next, an equimolar amount, 0.601 mg ethylenediamine/mL or 16.9 μL, was added to the reaction mixture, which was roller mixed for about 30 minutes further, to block aldehyde groups. A solution of 30 mg sodium borohydride in 3 mL of 1 mM potassium hydroxide solution was prepared, and 2.0 mL of this solution were pipetted into the particle suspension, which was roller mixed for another 30 minutes.

Gas was released after the reaction subsided in about 1 to 2 minutes. At the end of the reaction period the particles were separated by centrifugation for 5 minutes at 500 g, the supernatant was discarded, and the residue was washed four times with 1×PBS. 1×PBS was prepared by dissolving 53.8 g $K_2HPO_4$ in 1.6 L distilled water and adding 12.8 g $KH_2PO_4$ and stirring until dissolved. Then, 340 g NaCl was dissolved in the solution. After all salts are dissolved, distilled water was added to make up to 2 L volume and filtered through an 0.2 μm filter. The resulting solution is 20×PBS. 1×PBS is prepared by dilution of 1 part 20×PBS with 19 parts distilled water. The 1×PBS solution has a pH in the range 7.1–7.3, typically 7.2, a conductivity in the range of 13,500 to 15,500 $\mu$Mho-$cm^{-1}$ and is 0.15 M in NaCl. The final residue was resuspended to a total volume of 25 mL in 1×PBS.

B. Conjugation of T4/T8 Antibody to Crosslinked 5x-aminodextran-coated Silver-aminodextran-polystyrene Particles 4.5 μL of 10 mg/mL sulfo-SMCC per mL 1% w/v solids particles or 72.0 μL sulfo-SMCC solution was added to 16 mL of crosslinked 5x-aminodextran-silver-polystyrene particles in a 50 mL polypropylene centrifuge tube. The tube and contents were roller mixed for about one hour, after which the particles were separated by centrifugation for about 5 minutes at 500 g, the supernatant was discarded, and the residue was washed four times with 1×PBS, as described above. The final residue was resuspended to a total volume of 16 mL with 1×PBS.

10 mg each of T4 (0.225 mL) and T8 (0.266 mL) concentrate in 0.667 mL 1×PBS were separately activated with 2-iminothiolane (IT) at a 15:1=IT:antibody molar ratio, using 65 μL of 2 mg/mL IT solution. The reaction mixtures in 15 mL polystyrene centrifuge tubes were roller mixed for one hour, and then applied to the top of 50 mL G-50 Sephadex columns, equilibrated with 1×PBS. The columns were eluted with 1×PBS, and fractions of the first $A_{280}$-absorbing band containing IT-T4 or IT-T8 antibody were pooled to yield 2.6 mL of 2.351 mg/mL IT-T4 antibody and 3.0 mL of 2.709 mg/mL IT-T8 antibody.

Conjugations were run at 0.7 mg IT-T4 and 0.8 mg IT-T8/mL 1% w/v solids particles, so that 1.191 mL IT-T4/ 1.181 mL IT-T8 solution were added to duplicate samples of 4 mL of sulfo-SMCC-activated particle suspension and the mixtures were roller mixed for about two hours. At the end of the conjugation period, 1 mL of each conjugation reaction mixture was pipetted and filtered through an 0.2 μm low-protein binding filter disc. The $A_{280}$ of the supernatant was measured to yield a 0.504 mg/mL IT-T4/0.534 mg/mL IT-T8 concentration. By difference, the surface concentration of IT-T4 was 0.107 (0.084)mg/mL or 5.1 (4.0)mg T4 antibody/ $m^2$ of particle surface area and the surface concentration of IT-T8 was 0.391 (0.386) mg/mL or 18.7 (18.5) mg T8 antibody/$m^2$ of particle surface area, assuming smooth spherical 2 μm diameter particles of specific surface area, 2.7082 $m^2$/g.

Both T4- and T8-conjugated particles were divided into two 4.2 mL samples, one without blocking and the other with blocking with L-cysteine and iodoacetamide. The with blocking samples were blocked with 0.503 mL of 5 mg/mL L-cysteine solution in 1×PBS (about 15 minutes), and then, 0.563 mL of 20 mg/mL iodoacetamide solution in 1×PBS and 0.105 mL of 1 M borate buffer solution, pH 9.8 (30 minutes). At the end of the blocking reactions, all four particle samples were separated by centrifugation for about 5 minutes at 500 g, the supernatants were discarded, and the residues were washed two times with BSA buffer, 1% BSA/0.1% sodium azide in 1×PBS solution, resuspended in BSA buffer, roller mixed for about one hour, and stored in a refrigerator at about 5° C. for 16–24 hours. The samples were then further washed two times with BSA buffer and the total volume of each sample was adjusted to 3.2 mL to obtain 1% w/v solids suspensions based on uncoated latex particles.

Example 4—Crosslinking and Conjugation of the Colloidal Gold-aminodextran-polystyrene Particles A. Preparation of the Aminotrithiol Linker The cross-linker, $C_{12}H_{26}N_2OS_3$, was prepared substantially as described in Whitesell & Chang [*Science* 261, 73 (1993)] and stored as the protected ligand, N-tert-butoxycarbonyl spider triacetate.

Before use, 10 mg of protected ligand was dissolved in 5 mL of anhydrous methanol to give a colorless solution. 2.5 mL of concentrated hydrochloric acid (36.5–38.0%) was then added to the solution of protected spider. The mixture was refluxed in a 50 mL round bottom flask for about 5 hours to give a yellow solution having the odor of free sulfhydryl groups.

The acid-catalyzed hydrolysis mixture (final volume of 3.0 mL) of spider ligand was applied to the top of a Bio-Gel P-2 column, 1.1 cm×30 cm, and eluted with distilled water. Fractions of the first band absorbing at 280 nm were collected and tested for free sulfhydryl groups with Ellman's reagent, 5,5'-dithio-bis-[2-nitrobenzoic acid], (Pierce Chemical Co.) against a phosphate buffer blank.

The reagent reacted with free sulfhydryl groups to form a highly colored chromophore with an absorbance at 412 nm [J. C. Ellman, *Clin. Chem. Acta*, 28: 234–241 (1962)]. About fifteen minutes were allowed for development with Ellman's reagent.

For a quantitative determination of sulfhydryl groups, a standard curve was run for L-cysteine to determine the linear response range for the complex. Twelve deprotected ligand fractions of 56 mL total volume gave an $A_{412}$ reading of 0.549 or sulfhydryl concentration of 0.458 mM, representing a yield of 44%.

B. Preparation of Aminotrithiol Cross-Linked Gold-Amdex-PS Particles 4.950 mL of 0.33 M aminotrithiol linker in ethanol solution, was prepared as described above and was added to 15 mL of 1% w/v solids gold-1×-aminodextran-polystyrene particle suspension in distilled water in a 50 mL polypropylene tube. The tube and contents were roller mixed for 16 to 24 hours, whereupon the particles were separated by centrifugation for about 10 minutes at 200 g, the supernatant was discarded, and the residue was washed four times with 1×PBS. The final residue was suspended to a total volume of 15 mL with 1×PBS.

C. Conjugation of T4/T8 antibody to crosslinked Aminotrithiolate-coated gold-aminodextran-polystyrene Particles 1.50 µL of 10 mg/mL sulfo-SMCC solution in 1×PBS per mL of 1% w/v solids particles or 22.5 µL for 15 mL trial of particle suspension were added to particles in 50 mL polypropylene centrifuge tube, and roller mixed for about one hour. At the end of the reaction period the particles were separated by centrifugation for about 10 minutes at 200 g, the supernatant was discarded, and the residue was washed four times with 1×PBS. The final residue was resuspended to a total volume of 15 mL with 1×PBS, and divided into two 7.5 mL portions for each trial.

10 mg of each antibody, T4 and T8, were activated with IT and the IT-T4 and IT-T8 derivatives were purified in the same way as described in Example 3 above. Conjugations were run in a similar way with 0.7 mg IT-T4/mL 1% particles and 0.8 mg IT-T8/mL 1% particles in separate trials. 1 mL of each trial was pipetted to analyze for IT-Ab in the supernatants: 6.7 mg T4 antibody/$m^2$ and 9.5 mg T8 antibody/$m^2$, assuming smooth spherical 2 µm diameter particles with a specific surface area of 2.7082 $m^2$/g. Samples were further divided equally for without blocking and with blocking with L-cysteine and iodoacetamide. The particles were then separated by centrifugation for about 15 minutes at 200 g, the supernatants were discarded, and the residues were washed two times with 1% BSA/0.1% sodium azide in 1×PBS, resuspended in BSA buffer, roller mixed for about one hour, and stored in a refrigerator at about 5° C. for 16–24 hours.

The T4- and T8-conjugated particles were further washed two times with BSA buffer and resuspended to a total volume of 3.4 mL to make 1% w/v solids suspensions based on uncoated latex particles.

D. Multi-angle Doppler Electrophoretic Light Scattering Analysis (DELSA)

The presence of aminotrithiolate linker attached to the surface of gold-1×-aminodextran-polystyrene ("1×-Amdex-PS") particles of Example 4B was demonstrated by obtaining the mobilities of these particles and all their parent particles, raw PS aldehyde/sulfate, 1×-Amdex-PS (Example 1), and gold-1×-Amdex-PS (Example 2D) particles, as a function of the pH of each suspension of particles using multi-angle Doppler electrophoretic light scattering (DELSA) measurements [Laser Doppler Spectroscopy: Applications To Cell And Particle Electrophoresis, E. E. Uzgiris, *Adv. Colloid Interface Sci.*, 14:75–171 (1981)].

DELSA measurements of suspensions of aminotrithiolate-gold-1×-Amdex-PS particles (Example 4B) and their T4- and T8-antibody-conjugated particles (Example 4C) were made on a COULTER DELSA 440. These measurements were used to establish the identity and pH stability range of coated particles layer-by-layer on raw particles.

Mobility is directly related to surface charge of particles in aqueous suspension—the larger the charge, either positive or negative, the higher the mobility. This pH dependence of the mobilities is presented in FIG. 1 for all stages of coated particles. Prior to electrophoretic measurements the raw PS and 1×-Amdex-PS particles were suspended in distilled water; the gold-1×-Amdex-PS particles, in 0.01 M sodium citrate; the aminotrithiolate-gold-1×-Amdex-PS particles, in 1×PBS; and the T4- and T8-aminotrithiolate-gold-1×-Amdex-PS particles, in 1% BSA, 0.1% sodium azide in 1×PBS. For measurements, all particles were diluted from either 4 or 1% w/v solids to $4 \times 10^{-4}$ percentage w/v solids with 0.01 M aqueous potassium nitrate solution. The pH of the diluted particle suspensions was adjusted with 0.1 M aqueous potassium hydroxide or 0.1 M aqueous nitric acid solutions.

DELSA measurements were made by positioning the rectangular sample channel of 1.00 mm height at the stationary layer (0.16 mm) near the top of the channel. An electrophoretic standard, Coulter EMPSL7, was used to make final adjustments in positioning the sample chamber. A van Gils plot, $(H-h)^2/H^2$ versus mobility, where h is the depth in millimeters (0 to 1.00) from the top of the channel and H=0.50 mm, of mobilities of the EMPSL7 standard was rectilinear through most of the depth of the channel and was symmetric about the center axis of the channel. Some deviation occurred near the bottom of the channel at h greater than 0.95 mm or $(H-h)^2/H^2$ greater than 0.8. This showed full development of a parabolic, electroosmotic flow profile of the standard particles in the DELSA sample chamber. Other DELSA instrument parameters were chosen as follows: frequency range, 500 Hz; frequency shift, 250 Hz; current, 0.7 mA unless otherwise noted; on time, 2.0 s; off time, 0.5 s.

Conductivities of the particle suspensions ranged from 1.3 to 1.6 mS/cm. As shown in FIG. 1, aminodextran(1x-Amdex)-coated polystyrene aldehyde/sulfate latex particles show nearly constant mobility of about $-1$ cm$^2$/V-s in the pH 7 to 10 range of measurements, reflecting the presence of positively-charged protonated amino groups that have replaced some neutral aldehyde groups to counter the pre-existing negatively-charged sulfate groups on the surface of the latex particles.

The raw polystyrene aldehyde/sulfate latex particles were originally negatively-charged and as shown in FIG. 1 have a very high negative mobility of $-6$ to $-7$ cm$^2$/V-s in the pH 7 to 10 range. After gold colloid was introduced onto the 1x-Amdex-PS particles, the steep drop in mobility of the resulting particles from about $+2$ to $-4$ cm$^2$/V-s in the pH 4 to 6 range showed the presence of adsorbed citrate on gold-1x-Amdex-PS particles even after dilution of the particles with aqueous sodium nitrate solution. The acid dissociation constants of citric acid as reflected in the stepwise $pK_a$ values of 3.14, 4.77, and 6.39 at 20° C., albeit modified for adsorbed citrate, occur in the same pH region as the large drop in mobilities.

The electrophoretic mobility profile of aminotrithiolate-gold-1x-Amdex-PS particles showed the mobility of these particles in a range of $-0.6$ to $-3.5$ cm$^2$/V-s, and also the presence of an artifact at about $+0.3 \times 10^{-4}$ cm$^2$/V-s throughout the pH 4 to 10 range. This artifact was also present in the same position in mobility profiles of 1x-Amdex-PS and gold-1x-Amdex-PS particles, especially at low currents (applied electric field) less than 1 mA in the cell. Higher currents of 1 to 2.5 mA were needed to obtain electrophoretograms of the latter particle suspensions so that Doppler frequency shifts were greater than +/-10 Hz for the lowest scattering angle of 8.6°. The artifact was identified by its constant position in van Gils plots of particle mobility and its constant position near 0.0 Hz at all four scattering angles in the power spectrum of intensity versus Doppler frequency shift.

The mobility of aminotrithiolate-coated gold-1x-Amdex-PS particles was elevated slightly above the mobility of the parent gold-1x-Amdex-PS particles above pH 5.8, but was lowered below that of the parent particles at pH less than 5.8. This reflects the lower negative charge that the aminotrithiolate linker can attain by displacing tri-negatively charged citrate on a metal particle surface as a tri-negative trithiolate group. The terminal amino group will still retain a positive charge due to protonation in the pH 4 to 10 region. Also, manifested in the steep rise in mobility from $-3.3$ cm$^2$/V-s to $-0.6$ cm$^2$/V-s in the low pH range of 5.8 to 4.2 may be partial protonation of the thiolate groups. Sulfhydryl groups typically show $pK_a$ values in the 7 to 9 range. Whereas as shown in the mobility measurements, single sulfur atoms of thiolate groups attached to surface gold or silver atoms form very strong bonds and are not as easily protonated as either of the carboxylate oxygen atoms of the three carboxylate groups of citrate on colloidal gold or silver.

The features in the electrophoretograms of aminotrithiolate-gold-1x-Amdex-PS particles are reversible through several cycles of base addition to pH 10 followed by acid addition to pH 4.

The T4- and T8-antibody, conjugated aminotrithiolate-gold-1x-Amdex-PS particles show respective antibody-coated particles with nobilities in a much narrower and more positive +1.2 to $-2.3$ cm$^2$/V-s range than the parent particles. Also, the negative charge of the parent particles throughout the pH 4 to 10 range is counterbalanced but not dominated by the antibody, so that the point of zero charge ("p.z.c.") of the antibody-conjugated particles lies between pH 4.5 and 5.0, instead of the pI range of the monoclonal antibodies which is pH 5.4–5.8 for T4 antibody and pH 6.7–7.3 for T8 antibody as determined from the main bands for the respective antibodies by conventional gel electrophoresis. Storage of T4- and T8-conjugated particles in 1% bovine serum albumin ("BSA"), 0.1% sodium azide in 1xPBS buffer, before dilution with 0.01 M potassium nitrate solution may also produce by adsorption of BSA unto the particle surface a p.z.c. range overlapping with the pI of about 4.9 for BSA.

The silver-1x-Amdex-PS (Example 2A) particles showed only a slightly decreasing negative mobility ($-0.57$ to $-1.6$ cm$^2$/V-s) from pH 5 to 10, which is very similar to and only slightly negative of the mobilities of the parent 1x-Amdex-PS particles. This compares with mobility data obtained by the moving boundary method for the Carey Lea silver sol (about 10 nm mean diameter silver particles) washed with aqueous sodium citrate, which was reported at a zeta potential of $-80\pm5$ mV or mobility of $-3.7$ cm$^2$/V-s. (see G. Frens et al, *Kolloid Z.Z. Polym.*, 233:922 (1969)). Further, microelectrophoresis experiments with several silver sols, for example silver sol with sodium borohydride (Ag(NaBH$_4$)) at pH 8.1), silver sol prepared with ethylenediaminetetraacetic acid (Ag(EDTA)) at pH 10.1), Carey Lea silver sol (Ag (Carey Lea) at pH 7.0), and silver sol prepared in aqueous silver sulfate solution (Ag (aqueous AgSO$_4$ solution) irradiated with $^{60}$Co) at pH of about 5.7 gave mobilities between $-4.2$ and $-5.0$ cm$^2$/V-s , and with the red gold citrate sol (about 20 nm mean diameter gold particles) gave an electrokinetic mobility of $-4.5$ cm$^2$/V-s at pH of about 5.5 [Heard et al, *J. Colloid Interface Sci.*, 93:545 (1983)].

Although the gold-1x-Amdex-PS particles show a similar mobility of about $-4.0$ cm$^2$/V-s in the pH 6 to 9 range as the mobility of the gold citrate sol at pH of about 5.5, the mobility ($-0.6$ to $-1.6$ cm /V-s) of silver-1x-Amdex-PS particles does not resemble that ($-4.2$ to $-5.0$ cm$^2$/V-s) of silver citrate sols and suggests that silver-citrate bonding in the silver-1x-Amdex-PS particles was weak so that dilution of the particle suspension in 0.01 M potassium nitrate solution for the purpose of electrokinetic measurements released much of the originally adsorbed citrate on silver-1x-Amdex-PS particles.

Example 5—Analyses of the Crosslinked and Protein Coated Colloidal Metal-aminodextran Coated Particles The gold- or silver-coated polystyrene particles of Examples 3 and 4 were characterized by SEM micrographs of dried particles on a solid substrate, by flow cytometry histograms of forward scatter (FS) versus side scatter (SS), and for antibody-conjugated particles by specificity for targeted white blood cell sub-populations in whole blood according to angular light scattering and DC or RF conductivity matrices. Also examined were silver coated particles which were reacted with the aminotrithiol linker of Example 4A.

A. Flow Cytometry Analysis of the Cross-linked metal-Amdex-PS Particles and the Protein conjugated particles Flow cytometry of the particles of Example 3A showed 41% singlets, 51% multiplets, and 5% uncoated polystyrene particles.

Flow cytometry of the protein conjugated particles of Example 3B showed 64% singlets, 33% multiplets, and 1.4% uncoated polystyrene particles for T4-Amdex-Ag-Amdex-PS particles without blocking; 57% singlets, 41% multiplets, and 0.4% uncoated polystyrene particles for blocked T4-Amdex-Ag-Amdex-PS particles; 60% singlets, 38% multiplets, and 0.4% uncoated polystyrene particles for T8-Amdex-Ag-Amdex-PS particles without blocking; 56% singlets, 42% multiplets, and 0.3%, uncoated polystyrene particles for blocked T8-Amdex-Ag-Amdex-PS particles.

However, side scatter shifts in forward versus side scatter histograms obtained by flow cytometry for the silver coated particles cross-linked with the aminotrithioate linker in a manner similar to that described in Example 4B were not as large for silver-PS particles that had been reacted with ligand and tended to revert to the position of uncoated polystyrene particles in the histograms.

Flow cytometry of the cross-linked-gold-Amdex-PS particles of Example 4B showed 64% singlets, 23% multiplets, and 8% lightly-coated polystyrene particles.

Flow cytometry of the protein conjugated particles of Example 4C showed 82% singlets, 8% multiplets, and 10% lightly-coated polystyrene particles for blocked T4-aminotrithiol-Au-Amdex-PS particles; 75% singlets, 12% multiplets, and 13% lightly-coated polystyrene particles for T4-aminotrithiol-Au-Amdex-PS particles without blocking; 83% singlets, 5% multiplets, and 11% lightly-coated polystyrene particles for blocked T8-aminotrithiol-Au-Amdex-PS particles; and 73% singlets, 12% multiplets, and 15% lightly-coated polystyrene particles for T8-aminotrithiol-Au-Amdex-PS particles without blocking.

B. SEM Analyses

Figure 4A:
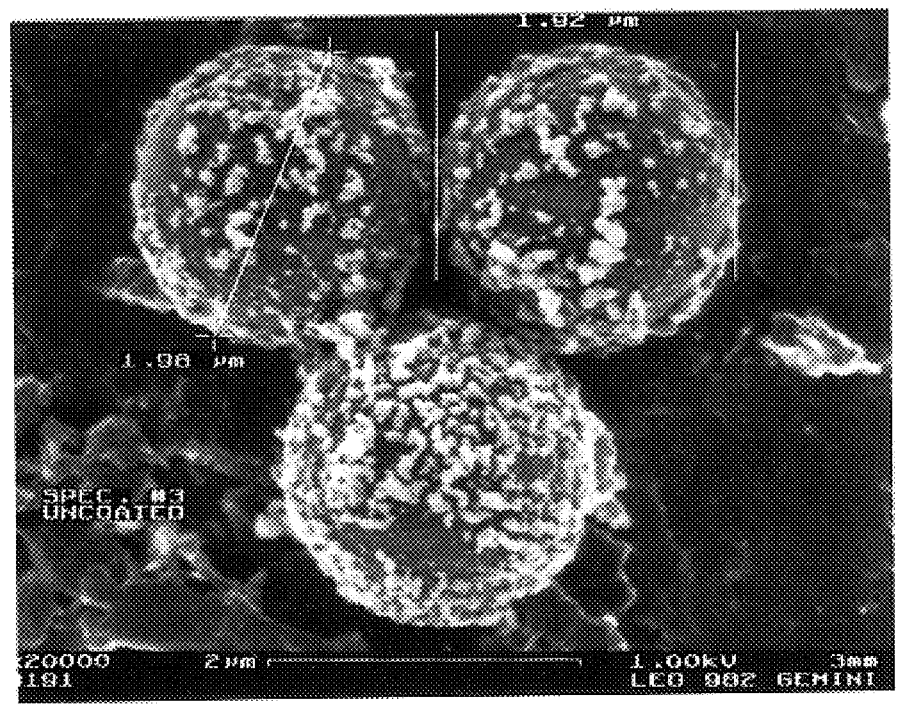
FIG. 4A is a scanning electron microscope (SEM) photograph of particles of the invention, comprising an T4 antibody linked via an aminotrithiol linker to a gold embedded, aminodextran coated, PS particle (T4-aminotrithiol-Au-Amdex-PS) at magnification x20,000.
Figure 4B:
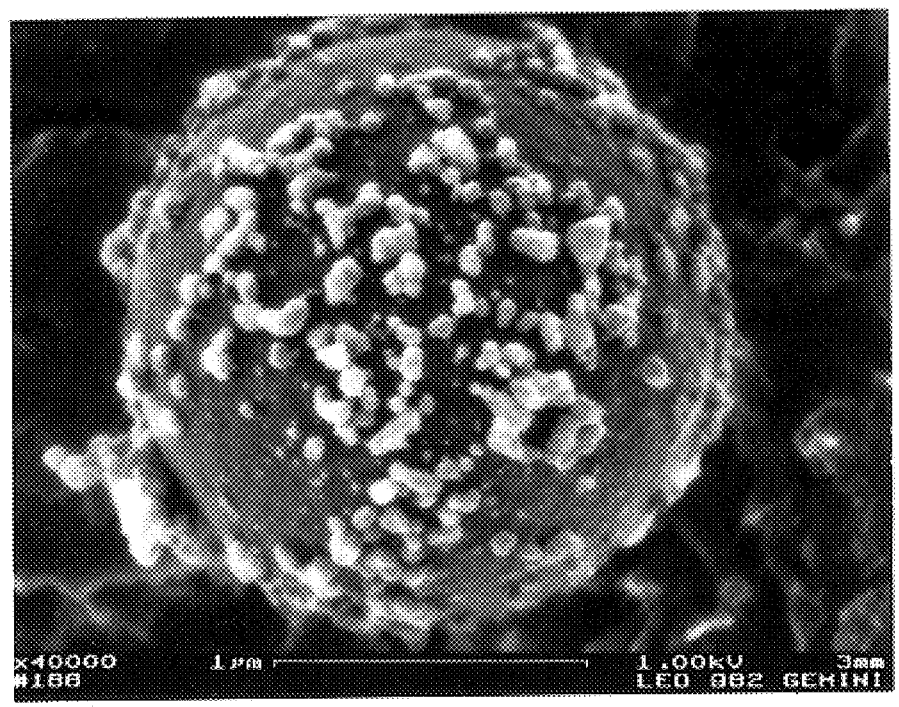
FIG. 4B is an SEM photograph of the particles of FIG. 4A at magnification x40,000.
Figure 4C:
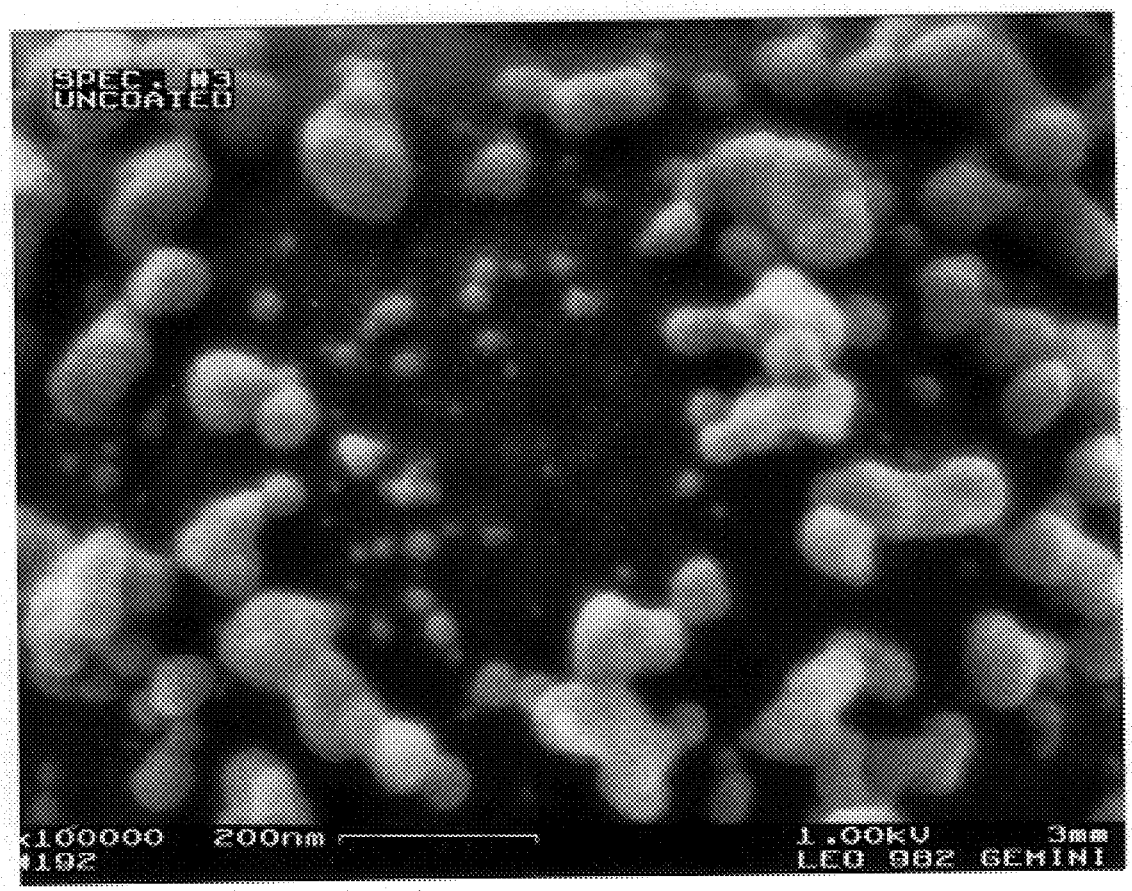
FIG. 4C is an SEM photograph of the particles of FIG. 4A at magnification x100,000.
Figure 5A:
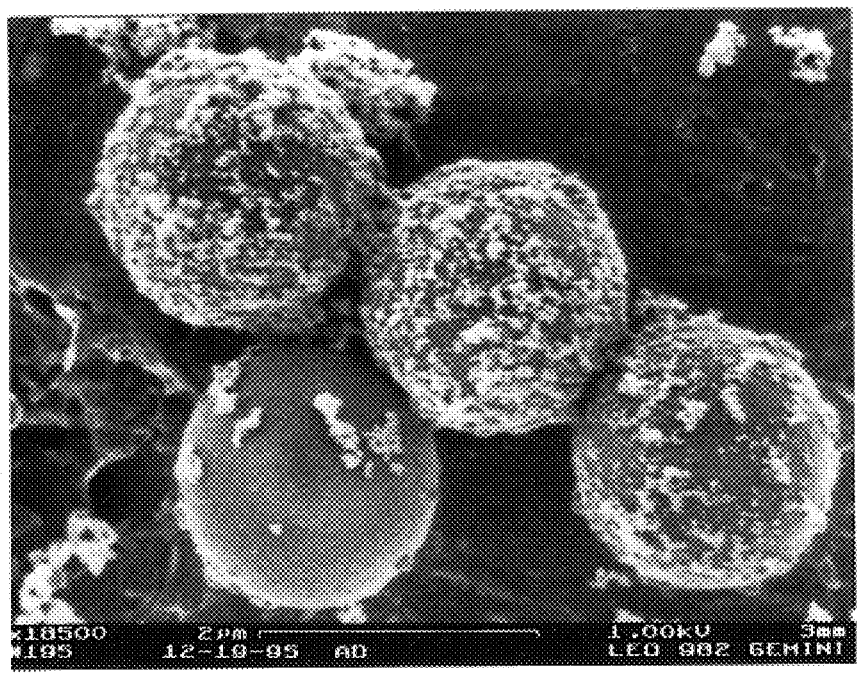
FIG. 5A is an SEM photograph of the particles similar to that of FIG. 4A, except that the metal colloid is silver (T4-Aminotrithiol-Ag-Amdex-PS) at magnification x18,500.
Figure 5B:
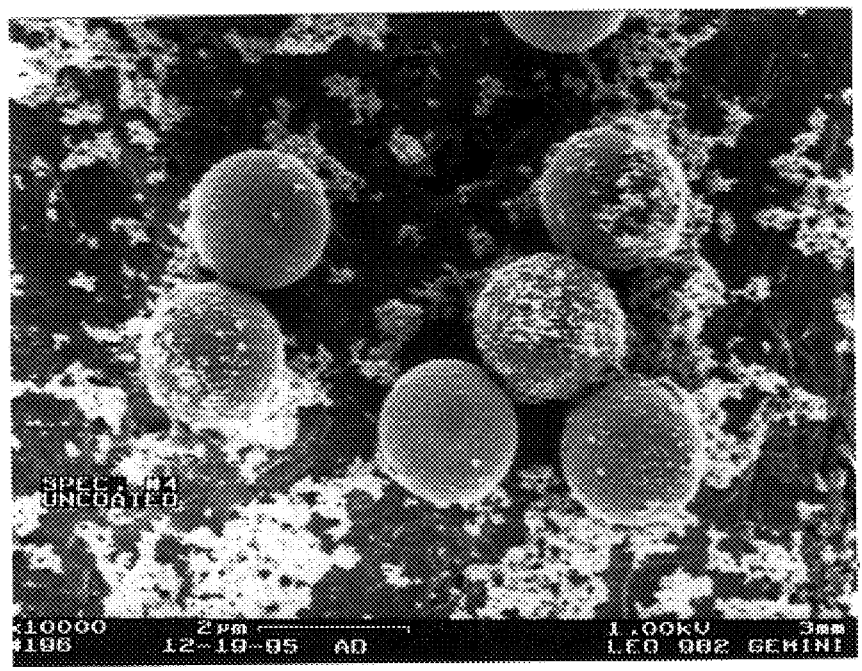
FIG. 5B is an SEM photograph of the particles of FIG. 5A at magnification ×10,000.
Figure 5C:
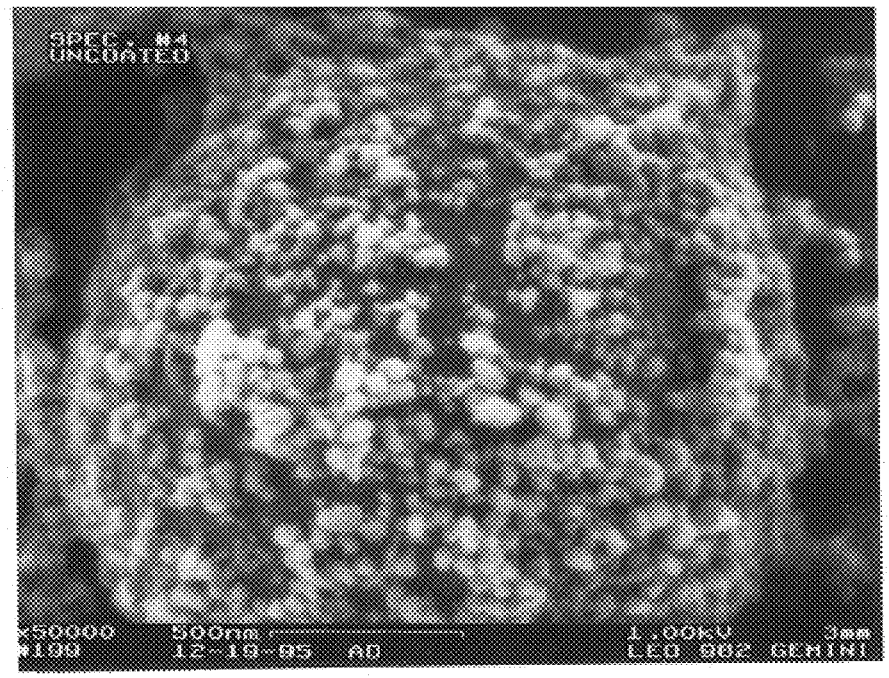
FIG. 5C is an SEM photograph of the particles of FIG. 5A at magnification ×50,000.
Figure 5D:
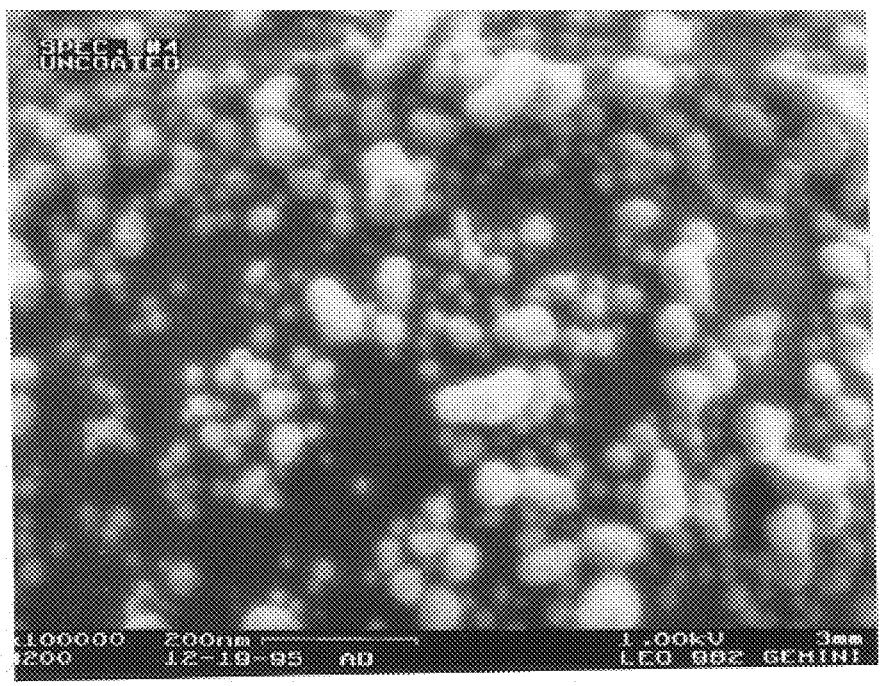
FIG. 5D is an SEM photograph of the particles of FIG. 5A at magnification ×100,000.
Figure 6A:
FIGS. 6A–6F illustrate matrices of the electronic sensing parameter (DC) versus Side Angle Light Scatter (SALS) for whole blood and various mixtures of whole blood with T4-Amdex-Ag-Amdex-PS particles, obtained with 633 nm excitation, demonstrating the progressively shifted SALS of targeted T4+ lymphocytes with increasing titers (2, 5, 10, 20, and 40 μL, respectively) of particles.
Figure 6D:
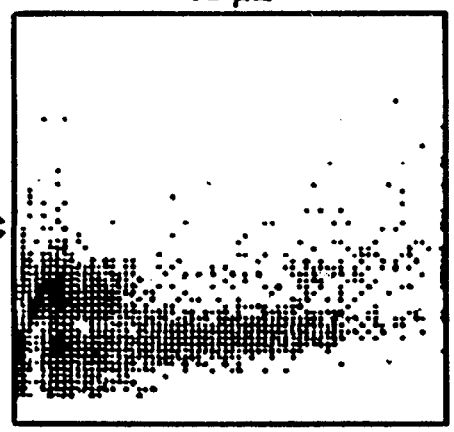
Figure 6B:
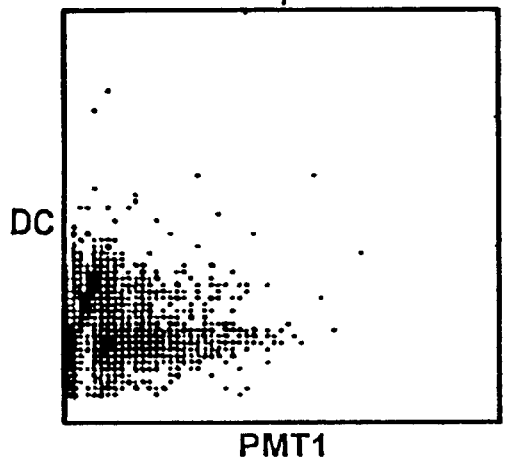
Figure 6E:
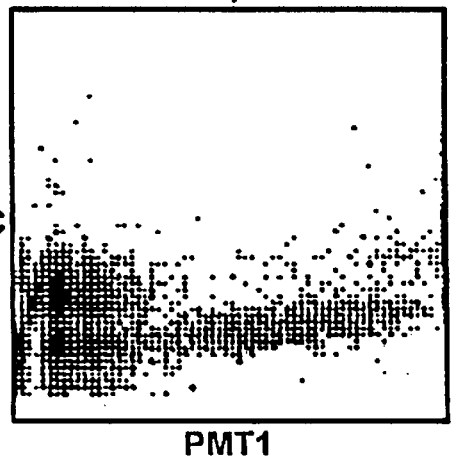
Figure 6C:
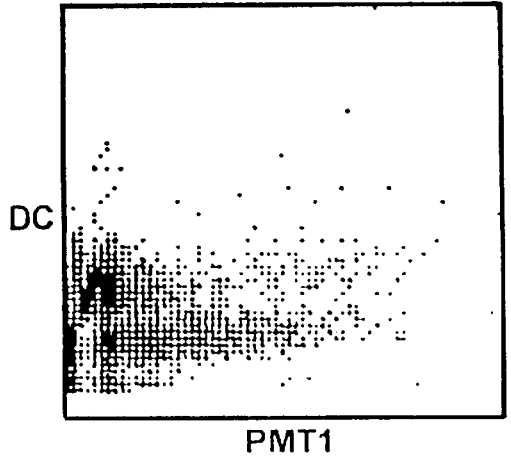
Figure 6F:
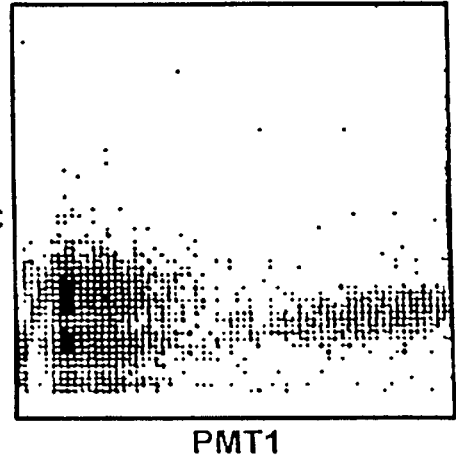
Figure 7B:
Figure 7D:
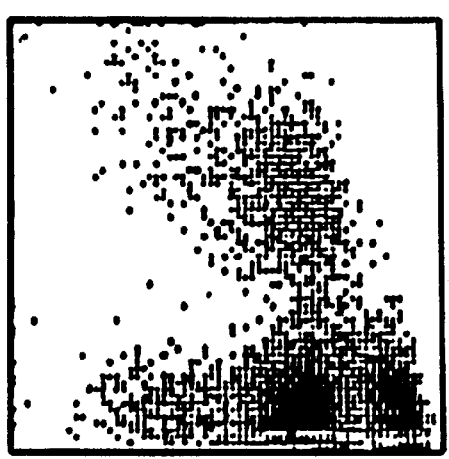
Figure 7A:
Figure 7C:
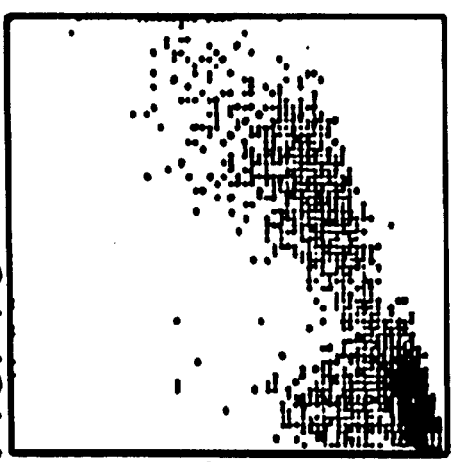
Figure 8J:
Figure 8L:
Figure 8I:
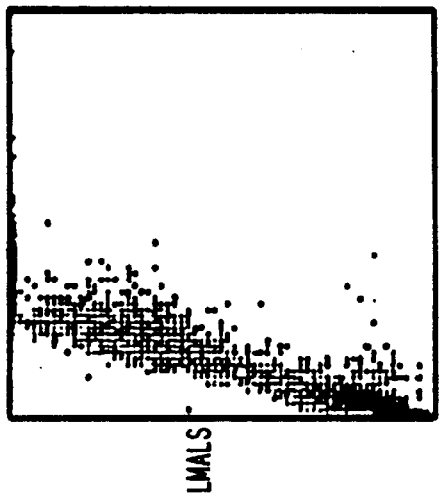
Figure 8K:
Figure 10D:
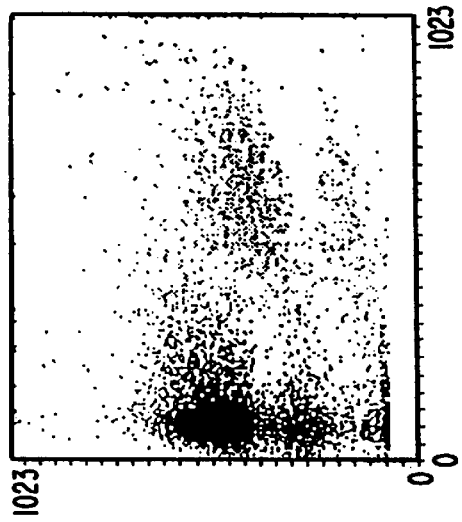
Figure 10E:
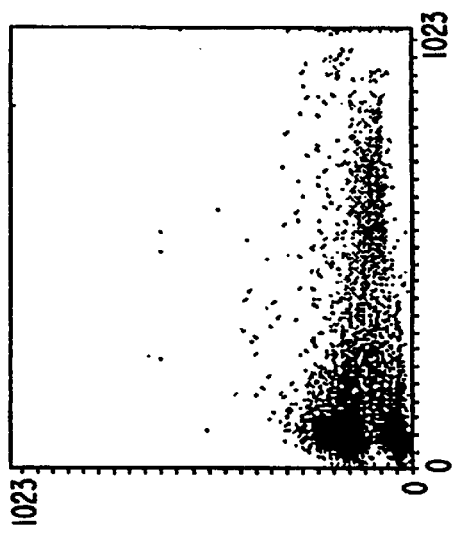
Figure 10F:
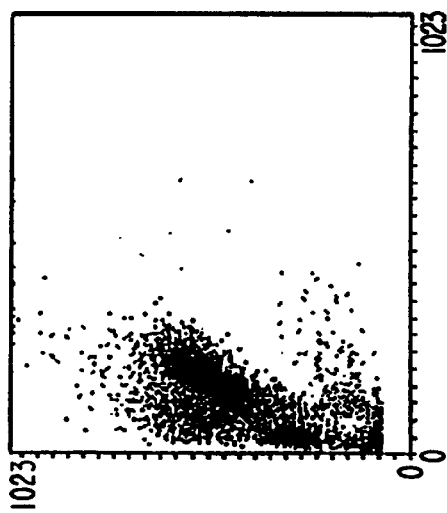
Figure 12D:
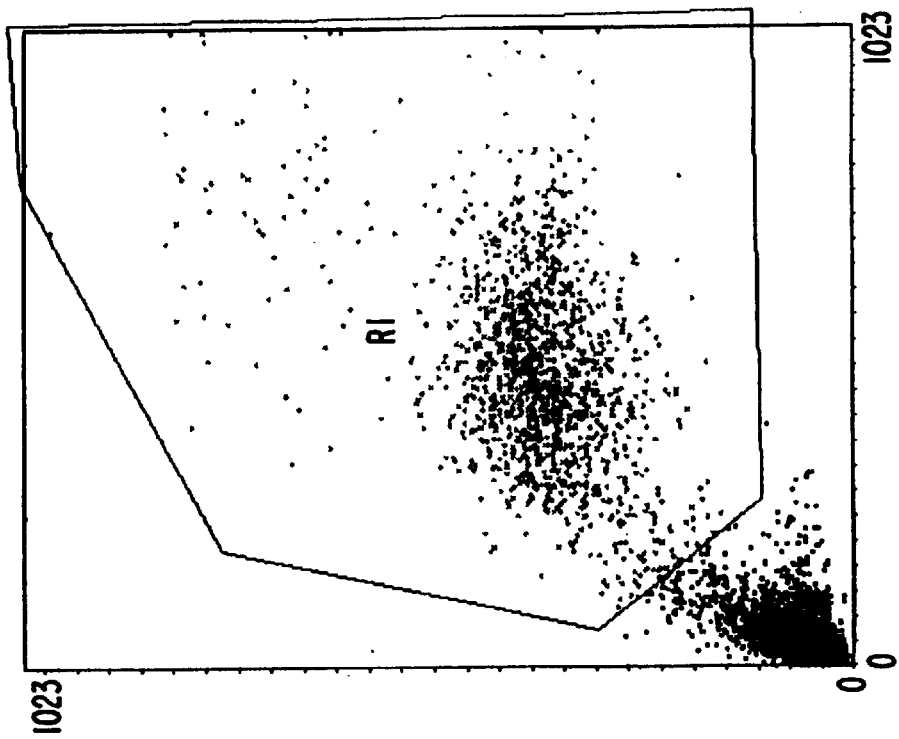
Figure 12C:
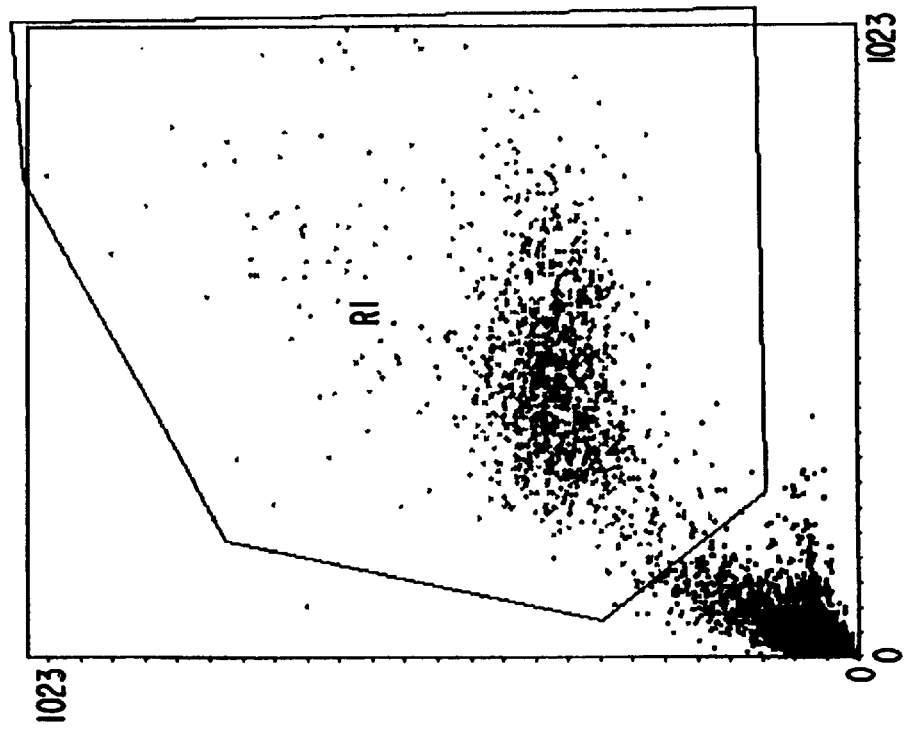
Figure 13A:
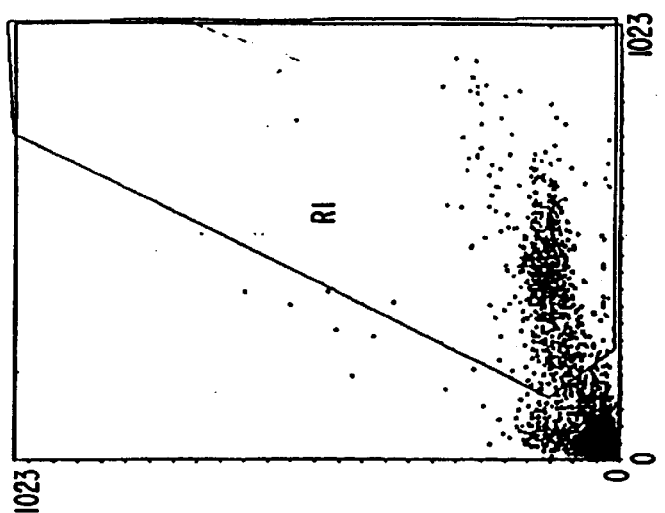
FIGS. 13A–13E show 90° LS versus UMALS matrices for mixtures of whole blood and five increasing titers of a T4-aminotrithiol-Au-Amdex-PS particle suspension, obtained with 633 nm excitation, showing the shifted location, R1, of T4+ lymphocytes in each matrix.
Figure 13B:
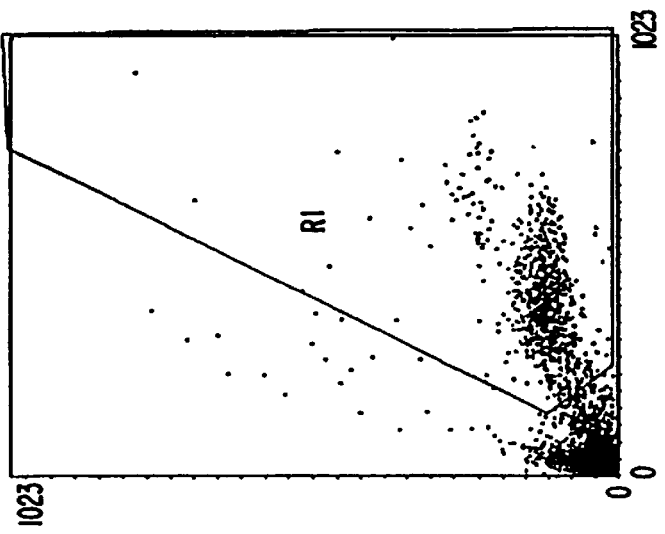
Figure 13C:
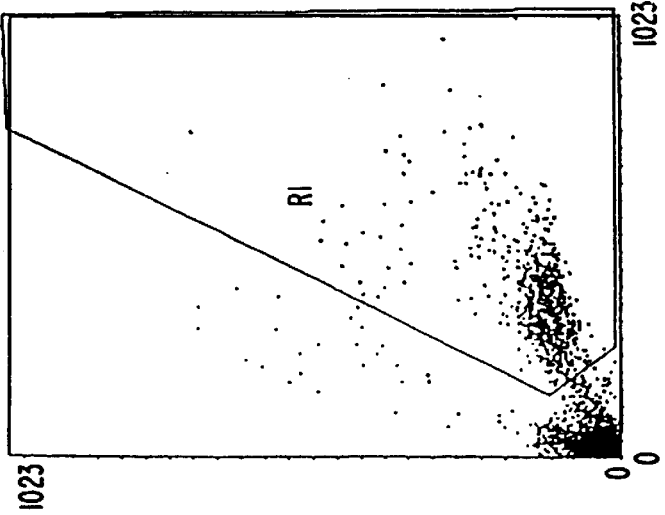
Figure 13E:
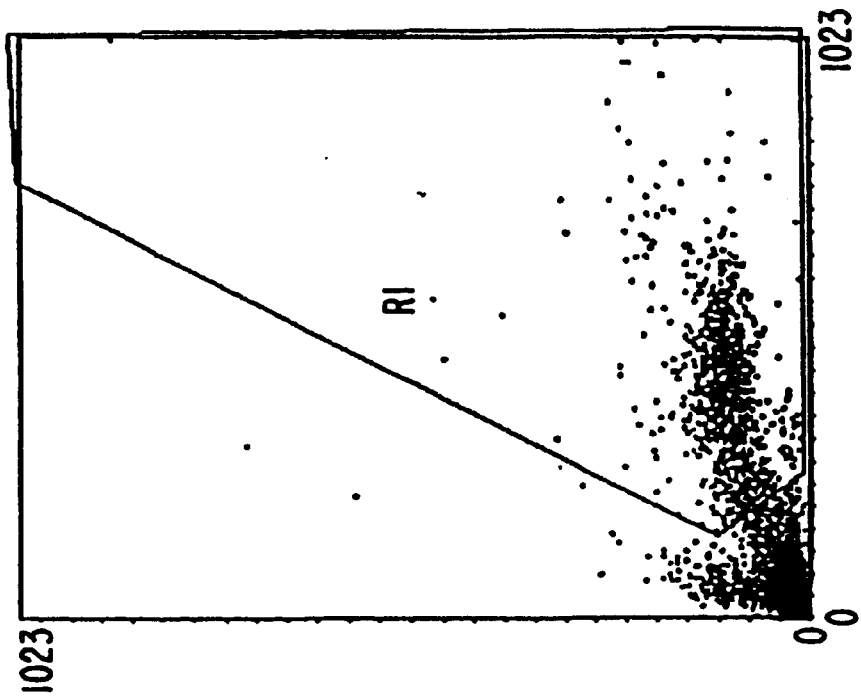
Figure 13D:
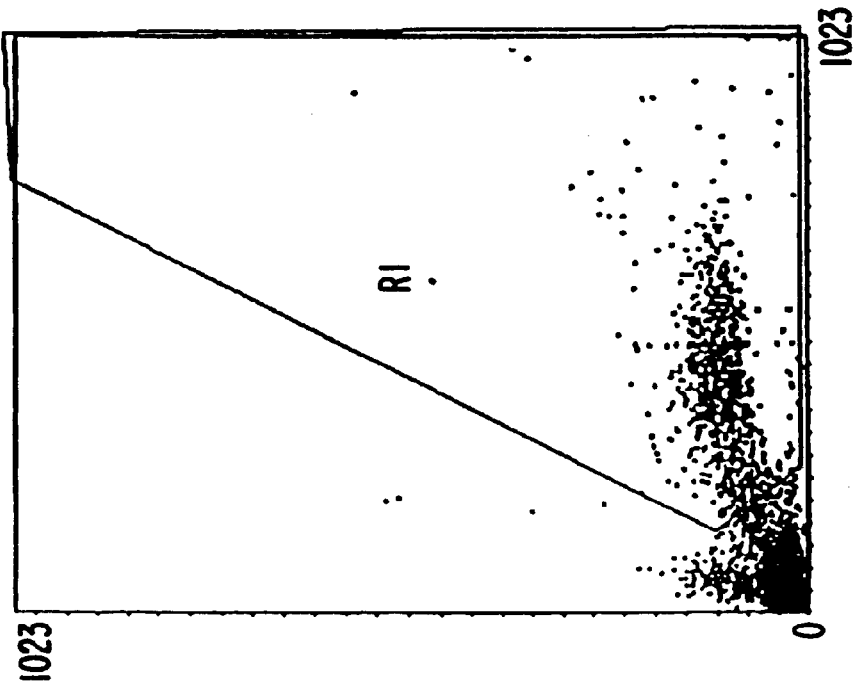
Figure 14A:
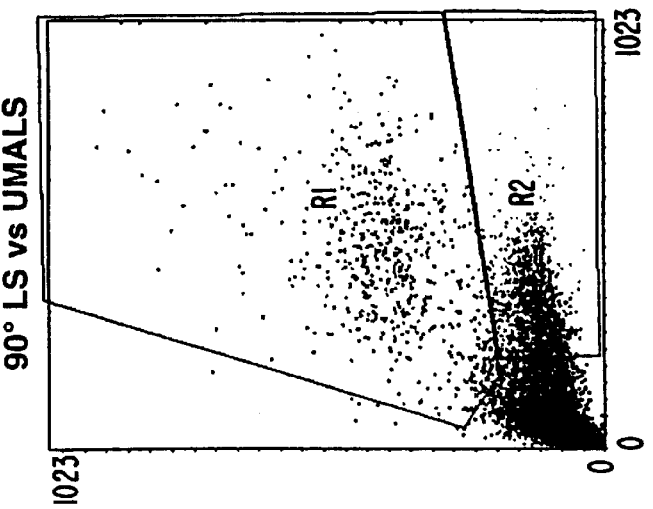
Figure 14B:
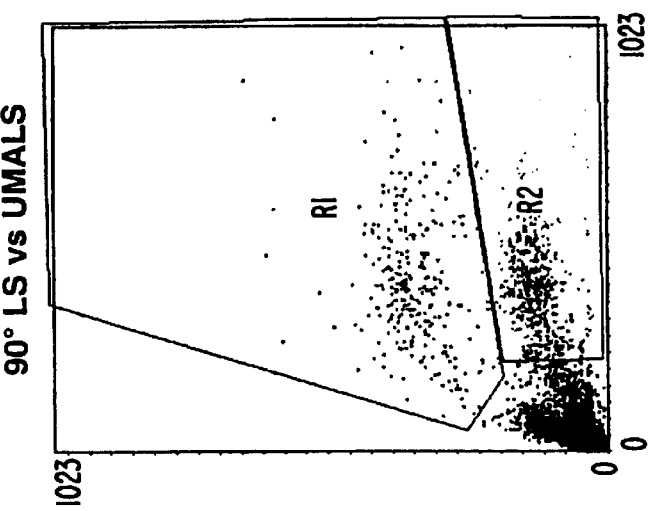
Figure 14C:
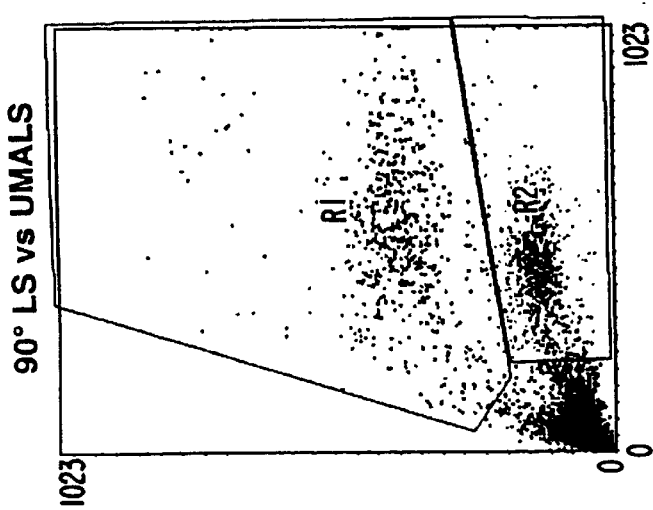
Figure 15C:
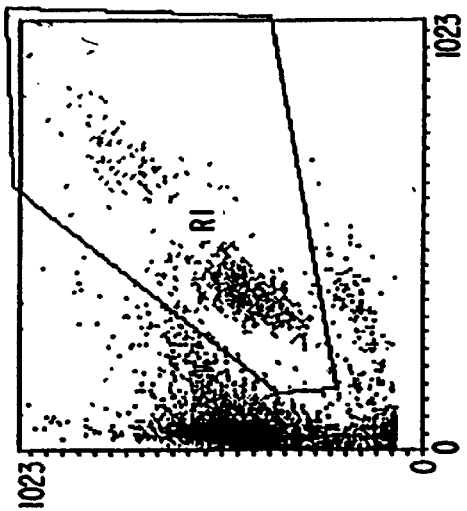
Figure 15B:
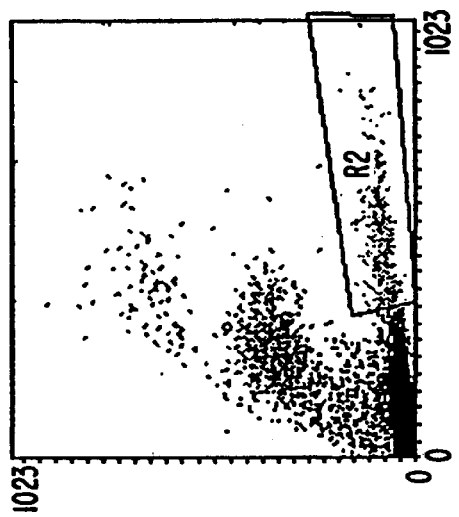
Figure 15A:
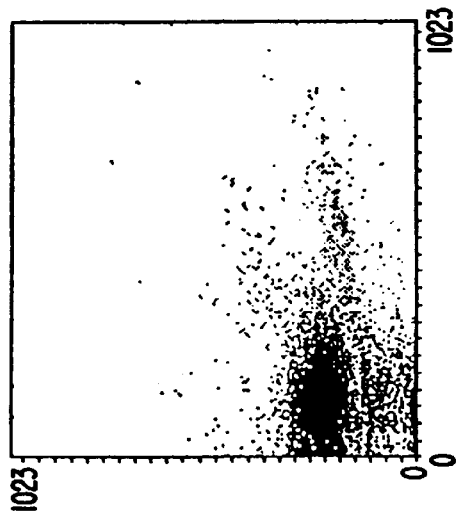

Scanning electron microscope (SEM) photos of T4-aminotrithiol-Au-Amdex-PS particles dried on a metal stub by evaporation of a small drop of suspension are shown in FIGS. 4A–4C. This shows a layer of gold colloid on polystyrene particles, as in original particles of gold deposited on the surface of polystyrene particles without being altered by binding of aminotrithiol linker, activation with sulfo-SMCC, conjugation with antibody, blocking, and washing with BSA buffer.

Silver-Amdex-PS particles were coated with aminotrithiol linker and conjugated with antibody in a similar way as for the above-described gold coated particles in Example 4. The aminotrithiol linker, however, competed too well with aminodextran for binding sites on the surface of deposited silver colloid on polystyrene particles and displaced much of the silver colloid from the surface of silver-aminodextran-polystyrene particles. This was seen from the opalescence of the supernatant of particle washings, which contained small silver particles. See the large bare spots on some particles and the presence of large aggregates of small silver particles in the SEM photos displayed in FIGS. 5A–5D. Apparently, the aminotrithiolate linker binds too strongly to the silver particles, dislodging them from their embedded positions in the aminodextran coating around the PS particles.

Also, the SEM micrographs of samples taken after reaction with ligand showed large aggregates of small silver particles and polystyrene particles with many bare spots, whereas the same particles were uniformly coated with silver colloid before reaction with ligand. Thus, aminotrithiol does not work well as a crosslinking agent with silver colloid on polystyrene particles.

Example 6—Conjugation of T4 and T8 Antibodies to Diaminopropane-coated Polystyrene Aldehyde/sulfate Latex Particles This example describes coated particles used as controls and as one of a pair of beads in simultaneous experiments to verify the results of the methods and compositions of the present invention.

A. Preparation of Particles

Except for the scale up preparation, coupling of 1,3-diaminopropane (DAP) to polystyrene latex particles was carried out by methods previously described in International Patent Application No. WO9524631, published Sep. 14, 1995.

To 1000 mL of 4% w/v solids polystyrene aldehyde/sulfate particles (Interfacial Dynamics Corp., about 2 μm diameter) in a 2 L polypropylene bottle were added 16.8 mg of liquid DAP (0.888 g/mL specific gravity) per mL of particle suspension or 19.1 mL DAP. The resulting suspension was mixed well by vortexing, sonicated for 30 seconds, and roller mixed for 24 to 72 hours. To reduce Schiff's base groups and unreacted aldehyde on the surface of the particles, 10 mg of solid sodium borohydride per mL of 4% w/v solids particles that were roller mixed with DAP, or 10.4 g were added directly to the particle reaction mixture. No excessive effervescence took place in the presence of excess DAP at a pH of about 11.5. The reaction mixture was roller mixed for about three hours with occasional brief 30 second sonication and release of hydrogen gas from the reaction vessel. The particles were then separated by centrifugation at about 2600 g for about 25 minutes. The supernatant was discarded and the residue of particles was resuspended in about 1 L distilled water.

Redispersion of the particles was accomplished by vortexing and brief sonication. The washing procedure by centrifugation was repeated four times and the final particle suspension was adjusted to 1000 mL total volume with 1×PBS solution.

Activation of DAP-coupled particles was accomplished with sulfo-SMCC. In general, 14.2 μL of freshly prepared 10 mg/mL sulfo-SMCC in 1×PBS was used per mL of 4% w/v solids DAP-coated polystyrene particle suspension. In a typical preparation, 14.2 mL of the sulfo-SMCC solution was added to 1000 mL of 4% w/v solids particles. The mixture was then roller mixed in a 2 L plastic bottle for about one hour, separated by centrifugation, and washed a plurality of times with 1×PBS solution.

The functionalized, DAP-coated particles resulting from the above series of steps have pendant maleimidyl groups and are suitable for conjugation to a variety of biological molecules. If the substance which is desired to be conjugated to the particles has a sufficiency of active sulfhydryl groups, activation of that substance is not necessary, and the following step may be skipped.

Antibodies were activated with 2-iminothiolane (IT) hydrochloride. In a typical run, a 42.77 mg/mL concentrate of T4 monoclonal antibody in 1×PBS containing 0.1% sodium azide was prepared. For 1000 mg T4 (or T8) antibody and 15 mg/mL antibody concentration during coupling, the total reaction volume should be 66.67 mL. Using a 15:1::IT:T4 activation ratio, 93.75 μmol (12.9 mg) IT (6.45 mL of 2 mg/mL IT) in 1×PBS is required. Therefore, 36.84 mL of 1×PBS solution was added to 23.38 mL of T4 concentrate, to which resulting solution an additional 6.45 mL of 2 mg/mL IT solution was added. The net resulting solution was roller mixed in a 250 mL centrifuge tube for 1 hour. The contents of the reaction tube were then applied to the top of a 2000 mL G-50 Sephadex column, equilibrated and washed with 1×PBS solution.

The derivatized antibody was eluted using 1×PBS and a plurality of 15 mL fractions were collected with the aid of a UV monitor. Fractions in the middle of the band absorbing at 280 nm were pooled and the $A_{280}$ value was used to determine the IT-T4 antibody concentration. Typically, the IT-T4 or IT-T8 concentration was 5–6 mg/mL.

The IT-T4 or IT-T8 was then conjugated with sulfo-SMCC derivatized particles. In a laboratory scale conjugation, total volume 1000 mL, the concentration of particles was 6.67% w/v solids and the IT-T4 concentration was 0.7 mg/mL or the IT-T8 concentration was 0.8 mg/mL. In one sample, when the purified IT-T4 solution concentration was 6.236 mg/mL, then 112 mL of IT-T4 antibody solution in 1×PBS and 288 mL of 1×PBS solution were added to 1000 mL of 4% w/v solids sulfo-SMCC activated particles which had been preconcentrated by the removal of 400 mL of supernatant.

In another sample, the purified IT-T8 antibody solution concentration was 5.846 mg/mL, so that 137 mL of IT-T8 antibody solution in 1×PBS and 263 mL of 1×PBS solution were added to 1000 mL of 4% w/v solids sulfo-SMCC activated particles which had been preconcentrated by the removal of 400 mL of supernatant. The IT-antibody solution was added to the particles in 25 mL increments with vortexing and ultrasonication between additions. The resultant mixture was then roller mixed in a 2 L bottle for about two hours.

Before blocking, 1 mL samples of the conjugation mixtures were pipetted, filtered through 0.2μm low-protein binding filter, and the absorbance of the supernatants was measured at 280 nm to obtain surface concentration of antibody, 0.44 mg/mL T4 and 0.53 mg/mL T8, and surface densities of 4.2 mg T4 antibody/m and 5.1 mg T8 antibody/m$^2$.

Unreacted maleimidyl groups on the sulfo-SMCC activated particles were blocked with L-cysteine after antibody conjugation. Typically, 120 mL of 5 mg/mL L-cysteine in 1×PBS were added to the conjugation mixture of the previous step and the resulting suspension was roller mixed for about 15 minutes. Unreacted sulfhydryl groups were blocked by the addition of 134 mL of 20 mg/mL iodoacetamide in 1×PBS followed by the addition of 25 mL of 1 M, pH 9.8 sodium borate buffer solution. The resulting suspension was roller mixed for about 30 minutes, the blocked conjugation mixture was separated by centrifugation and the particles washed two times with a solution of 1% bovine serum albumin (Pentex fraction V, protease free) and 0.1% sodium azide in 1×PBS (BSA buffer solution). After washing, the particles were resuspended in BSA buffer solution to a total volume of 1000 mL (4% w/v solids), roller mixed for about 1 hour, stored at about 4° C. for a time in the range of 24–72 hours, separated by centrifugation and washed three times with BSA buffer solution.

B. Analysis of Particles

Flow cytometry of particles alone in 1 mM KOH solution gave 87.2% singlets, 11.6% doublets, and 0.6% multiplets for T4 particles and 94.3% singlets, 5.1% doublets, and 0.1% multiplets for T8 particles.

C. DELSA Analysis

Figure 2:
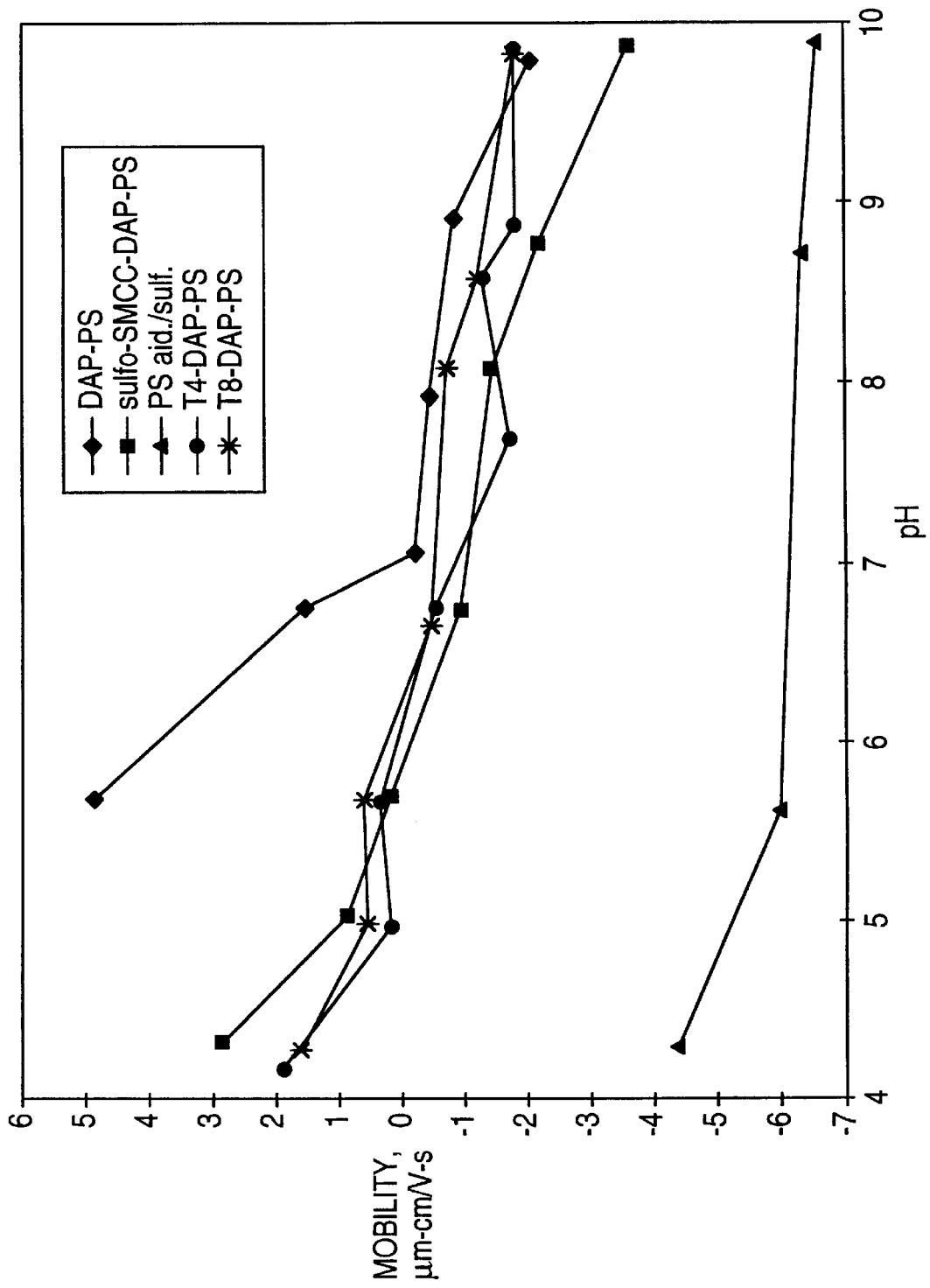
FIG. 2 is a graph plotting the electrophoretic mobility versus pH data for suspensions of aldehyde/sulfate PS, uncoated or coated with 1,3-diaminopropane (DAP), sulfo-succinimidyl 4-[N-maleimidomethyl]cyclohexane-1-carboxylate (sulfo-SMCC), and T4 or T8 antibody, all washed with 1x phosphate buffered saline (PBS) only.
Figure 3:
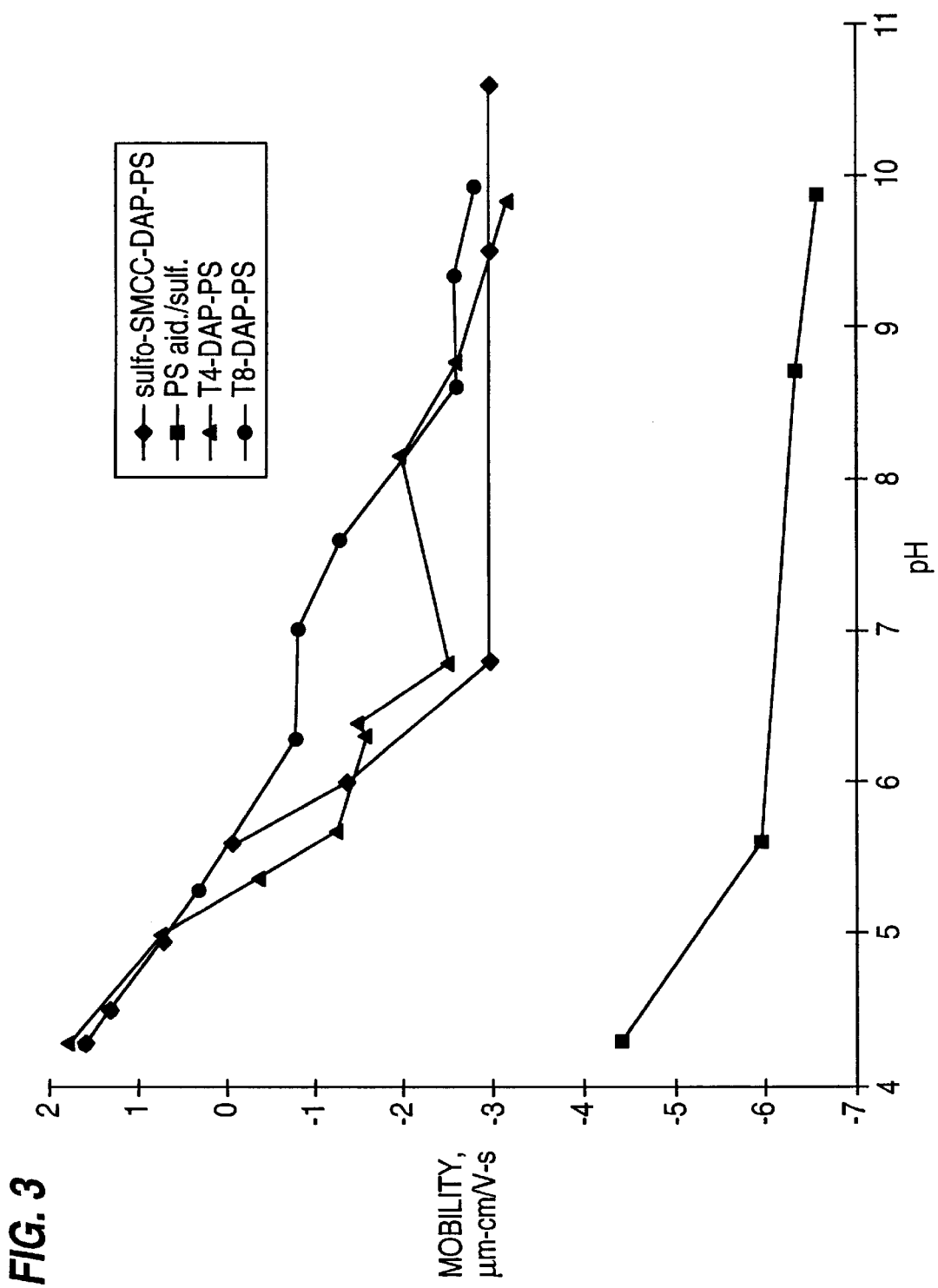
FIG. 3 is a graph plotting the electrophoretic mobility versus pH data for suspensions of aldehyde/sulfate PS, uncoated or coated with sulfo-SMCC-DAP and T4 or T8 antibody, all washed with bovine serum albumin ("BSA") buffer and 1xPBS.

The T4- and T8-antibody conjugated to diaminopropane (DAP)-coated polystyrene aldehyde/sulfate particles as described above were also investigated for their electrokinetic properties. DELSA measurements of mobility as a function of pH were also made of DAP-PS (1×PBS wash), sulfo-SMCC-DAP-PS (w/blocking and 1×PBS wash), T4-DAP-PS (1×PBS wash), and T8-DAP-PS (1×PBS wash) particles. The mobility versus pH profiles of raw particles, DAP-PS particles, sulfo-SMCC-DAP-PS particles, and T4- and T8-DAP-PS particles are compared in FIG. 2, in order to provide evidence for the existence of the specified, coated particles according to expectations of charge on each particle derivative. The results in FIG. 2 are for 1×PBS washed particles and in FIG. 3 for BSA buffer and 1×PBS washed particles.

The raw particles were suspended in distilled water whereas the other derivatized particles were all washed with and suspended in 1×PBS before dilution with 0.01 M potassium nitrate solution for electrokinetic measurements.

The DAP-PS particles showed excellent surface coverage of positively-charged amino groups to compensate for the highly negative charge of raw particles, with mobilities between $-2.2$ and $+4.9 \times 10^{-4}$ cm/V-s in the pH 10 to 5.5 range and a p.z.c. of about pH 6.95. The positive charge of DAP-PS particles is somewhat reduced when sulfo-SMCC is used to activate amino groups for antibody conjugation to give mobilities of $-3.6$ to $+2.9 \times 10^{-4}$ cm$^2$/V-s in the pH 10 to 4 range and a p.z.c. of about pH 5.80. T4- and T8-antibody-conjugated DAP-PS particles assume electrokinetic properties intermediate to DAP-PS and sulfo-SMCC-DAP-PS particles with p.z.c. between 5.9 and 6.2.

Particles that had first been washed with BSA buffer and then with 1×PBS showed a modified mobility versus pH dependence (FIG. 3), with p.z.c. in the pH 5.3 to 5.6 range, closer to the pI of BSA at 4.9.

Example 7—Individual Analyses of Lymphocyte Subpopulations

Each particle was tested singly with whole blood to permit separate determinations of CD4 or CD8 positive cells in white blood cell population of whole blood, i.e., to determine the location of shifted target populations in the various histograms. For both individual and simultaneous analyses of T4 and T8 cell populations in whole blood, the particles used contained T4 and T8 antibodies conjugated to gold-coated PS particles, or silver- coated PS particles, and diaminopropane (DAP)-coated PS aldehyde/sulfate particles. The latter particles are preferred for accuracy as bead controls because they form fewer aggregates. All measurements in Example 7 and Example 8 were made with DAP-PS for comparison and controls.

A. Using (T4 or T8) -Amdex-Silver-Amdex-PS Particles

Separate analyses of the percentage of CD4 and CD8+ cells were made on a modified Coulter VCS instrument using T4 or T8-conjugated, silver-coated polystyrene particles of the invention (Example 3B) or T4 or T8-conjugated polystyrene particles without a metal coating. Coulter VCS technology, which allows measurement of volume, conductivity, and light scatter characteristics of blood cells, was used on the STKS2B hematology analyzer to assay for CD4 and CD8 cell populations in whole blood samples. Daily calibration of the analyzer was performed with COULTER LATRON primer and LATRON control.

Titers of 1% w/v solids T4-Amdex-Ag-Amdex-PS particles between 2 and 40 $\mu$L were mixed with 200 $\mu$L of whole blood for about 2 minutes. The mixtures were analyzed on the modified VCS instrument.

DC versus SALS (PMT1) matrices are shown in FIGS. 6A–6F for the blood sample and various mixtures. Note the successively greater shift of targeted T4 positive lymphocytes to higher SALS intensity as a larger titer of particles was used. The standard 20 $\mu$L titer appeared to be sufficient to resolve shifted from unshifted lymphocytes with either T4-DAP-PS or T4-Amdex-Ag-Amdex-PS particles.

Particle-to-cell ratios for targeted cell populations can be easily calculated and compared with theoretical values. For an average 45% CD4+ lymphocytes out of 2.4–6.8×10$^5$ lymphocytes per 200 $\mu$L of whole blood, there are 1.1–1.3× 10$^5$ CD4+ cells. For 2 $\mu$m diameter particles at 4% w/v solids, there are 6.83×10$^9$ particles/mL, so that the standard titer of 20 $\mu$L of 1% w/v solids particles per 200 $\mu$L of whole blood contains 3.4×10$^7$ particles. The range of particle-to-cell ratio is then 110–310.

Thus, FIGS. 6A–6F illustrate that the more particles added the greater the shift obtained. It also shows that a minimum of 20 $\mu$L titer is needed in order to obtain a good separation from shifted to unshifted of targeted cells.

A theoretical limit for a monolayer coating of particles around lymphocytes can be estimated for comparison. For lymphocytes of 8–12 $\mu$m diameter size range, the surface area assuming a spherical shape is $4\pi r^2$ or 201–452 $\mu m^2$. Thus, the maximum number of 2 $\mu$m diameter particles that can be packed around a single lymphocyte in a square lattice will range from 50 to 113. In a closest-packed lattice the area per particle is $\sqrt{3}\,d^2/2$ instead of $d^2$, so that the maximum particle-to-cell ratio will range from 58 to 130. The latter range was borne out almost stoichiometrically by an experiment when T4-DAP-PS particle titer runs showed that 10 $\mu$L of 1% w/v solids particles, or a range of particle-to-cell ratio from 55 to 155 was sufficient in almost every trial, whereas 5 $\mu$L was not always enough.

Similar results could be derived for T8-PS particle-to-cell ratios. For an average 20° CD8+ lymphocytes, the range of particle-to-cell ratio is 124–349 for a 10 $\mu$L titer of 1%-2 $\mu$m diameter particles so that about 2× more particles than theoretically calculated are needed.

The titer of particles needed may have to be increased for silver coated PS particles mixed with whole blood to compensate for the substantial numbers of particle aggregates containing more than two particles arranged in a non-linear geometric structure. Also, other factors, such as the immobilized antibody-cell surface antigen affinity constant, the number of specific antigenic receptors per targeted cell, and the accessibility of antigenic receptors on cells to immobilized antibody, can influence the required particle-to-cell ratio.

The affinities of T4 and T8 antibodies for their antigenic partners on the surface of T lymphocytes are very high, $10^{10}$ to $10^{12}$ M$^{-1}$ for T4, and $10^8$ to $10^9$ M$^{-1}$ for T8, so that binding is not a limiting factor [Oonishi et al, *J. Immunol. Methods*, 115:159 (1988); see also, U.S. patent application Ser. 08/624,014, filed Mar. 27, 1996, by Siiman et al]. Also, receptor per cell values range from $10^4$ to $10^5$ for CD4 and CD8 antigens, which project sufficiently from the surface of cells to offer excellent contact with potential immobilized antibody partners [R. F. Vogt, Jr. et al, *Cytometry*, 12:525 (1991); A. N. Barclay et al, *The Leukocyte Facts Book*, Academic Press, San Diego, Calif., (1993)].

Comparison of the lymphocyte population shifts due to T4-Amdex-Ag-Amdex-PS or T4-DAP-PS particles were made for various pairs of parameters and for excitation wavelengths of 633 nm and 780 nm in the matrices shown in FIGS. 7A–7L and FIGS. 8A–8L. The matrices with the best resolution of T4-Amdex-Ag-Amdex-PS shifted lymphocytes from T4-DAP-PS shifted lymphocytes are SALS (PMT1) versus LMALS or UMALS. Thus, for simultaneous analyses using multiple antibody labels, the best matrices to use are SAL(PMT1) versus LMALS or UMALS.

B. Using Protein Conjugated Particles of the Invention

Separate determinations of the percentage of CD4 or CD8 positive cells in a white blood cell population of whole blood were performed on a modified COULTER VCS instrument using T4 or T8-conjugated, gold- and silver-coated polystyrene particles of the invention or (T4 or T8)-DAP-PS particles not having a metal coating.

For percentage CD4/CD8 determination, 40 $\mu$L or 60 $\mu$L of a 1% w/v solids particle suspension was mixed with 400 $\mu$L of EDTA-anticoagulated whole blood for about 2 minutes in a 5 mL glass tube on a Coulter model 6705473 single speed mixer. In the manual mode, 150 $\mu$L of the whole blood-particle mixture were aspirated into the analyzer, which performed an automated acid lyse of red blood cells and quench, immediately after completion of mixing. The mixture was analyzed for various light scatter (SALS, UMALS, LMALS) parameters and DC and RF conductivity of the particle labeled and unlabelled white blood cells. Representative matrices for T4 particles are shown in FIGS. 9A–9F, 10A–10F and 11A–11F.

T4(T8)-DAP-PS particles showed the best separation of the targeted cell population in 90° LS versus RF, UMALS, DC, or LMALS and UMALS versus DC matrices. T4(T8)-conjugated, gold- or silver-coated polystyrene particles showed good separation only in 90 LS versus RF, UMALS, DC, or LMALS matrices.

Quantitation of percentage CD4 and percentage CD8 from 90° LS versus UMALS matrices was checked with T4(T8)-DAP-PS particles, 40 $\mu$L of 1% w/v solids, and 400 $\mu$L of whole blood from four normal donors in triplicate. Parallel determinations were made with the same particles and blood donors on the COULTER STKS® hematology analyzer. Flow cytometry was also used to obtain comparative results for percentage of CD4/CD8 positive cells in lymphocytes with the appropriate fluorescent antibody markers: Mouse IgG1-phycoerythrin/Mouse IgG1 Fluorescein Isothiocyanate ("MsIgG1-PE/MsIgG1-FITC"); or the dual fluorescence markers T3-FITC/T4-PE and T3-FITC/T8-PE (all from Coulter Corporation) for each donor. Table I shows the summarized results as percentages of CD4/CD8 positive cells in whole blood for four donors using T4 (T8)-DAP-PS.

TABLE I

Percentage CD4, CD8 Positive Cells in Whole Blood

| Donor: | 46848 | | 53522 | | 53960 | | 54152 | |
|---|---|---|---|---|---|---|---|---|
| % in wbc: | % CD4 | % CD8 | % CD4 | % CD8 | % CD4 | % CD8 | % CD4 | % CD8 |
| Trial 1 | 10.96 | 3.88 | 14.10 | 5.16 | 13.59 | 8.15 | 13.99 | 8.64 |
| Trial 2 | 9.94 | 3.37 | 14.33 | 5.25 | 13.16 | 8.33 | 14.36 | 8.82 |
| Trial 3 | 8.82 | 3.18 | 14.18 | 5.66 | 12.66 | 8.32 | 14.40 | 8.68 |
| Mean | 9.91 | 3.48 | 14.20 | 5.36 | 13.14 | 8.27 | 14.25 | 8.71 |
| % L in wbc: | 18.9 | | 27.6 | | 30.1 | | 27.8 | |
| % in L, mod. VCS | 52.42 | 18.40 | 51.46 | 19.41 | 43.64 | 27.46 | 51.26 | 31.34 |
| STKS % | 54.3 | 17.3 | 50.9 | 19.2 | 39.8 | 25.3 | 49.5 | 33.1 |
| flow % | 56.1 | 17.6 | 49.3 | 20.5 | 38.6 | 28.1 | 50.1 | 32.6 |
| % diff, mod. VCS-flow | 6.56 | 4.54 | 4.38 | 5.32 | 13.0 | 2.28 | 2.31 | 3.86 |

Representative 90° LS versus UMALS matrices for each blood donor are shown in FIGS. 12A–12D for T4-DAP-PS particle-whole blood mixtures. Donor 53960 appeared to indicate the presence of more cells bordering the gate in the bottom left-hand corner of the matrix between shifted and unshifted white blood cell populations. CD4 positive monocytes with very few particles have sometimes been identified in this region. For this donor, moving the gate slightly to higher 90° LS and higher UMALS gave an average 12.25% CD4 cells in white blood cells or 40.71% CD4 cells in lymphocytes, which gave only a 2.29% difference with the flow cytometry comparator.

Further, to establish the optimum amount of particle suspension, titers ranging from 10 to 80 $\mu$L of 1% w/v solids, T4(T8)-aminotrithiol-Au-Amdex-PS particles were mixed with 400 $\mu$L of whole blood for three donors and analyzed in the 90° LS versus UMALS matrices for percentage CD4 (percentage CD8) cells in the white blood cell population. Results are tabulated in Table II, showing the particle titer dependence of the percentage of CD4/CD8 positive cells in whole blood for three donors. The titer matrices are shown for representative donor 49070 in FIGS. 13A–13E for T4-aminotrithiol-Au-Amdex-PS particles.

established previously for 1% w/v solids T4 (T8)-DAP-PS particles of the same size, for which a 20 $\mu$L per 200 $\mu$L of whole blood was chosen as a standard titer. Thus, 60 $\mu$L of 1% w/v solids T4(T8)-aminotrithiol-Au-Amdex-PS particles per 400 $\mu$L of whole blood was chosen hereafter as the standard titer. For each donor the percentage of lymphocytes in the white blood cell population was obtained on the COULTER STKS hematology analyzer; thereafter, the percentage CD4/percentage CD8 in white blood cell obtained using the respective antibody-aminotrithiol-Au-Amdex-PS and antibody-DAP-PS particles were converted to percentages in L to compare with flow cytometry data with fluorescent markers and STKS data with PS particles.

Donors 50184 and 53608 have low percentages of lymphocytes in white blood cell, which are out of the normal range of 20–55%. These donors also showed the largest deviations in percentages of CD4/CD8 determined on the modified VCS versus comparative results obtained on the STKS hematology analyzer for T4/T8 particles mixed with whole blood or obtained by flow cytometry with the appropriate fluorescent markers.

The most useful matrices in this application were (i) SALS versus LMALS or UMALS, (ii) UMALS versus DC,

TABLE II

Particle Titer Dependence of Percentage CD4, CD8 Positive Cells in White Blood Cells

| Donor | 49070 | | 50184 | | 53608 | |
|---|---|---|---|---|---|---|
| Particle Titer, $\mu$L | % CD4 | % CD8 | % CD4 | % CD8 | % CD4 | % CD8 |
| 10, T4(T8)-Au-PS particles | 8.40 | 4.78 | 3.42 | 2.25 | 6.02 | 5.24 |
| 20 | 9. 65 | 4.29 | 4.34 | 2.42 | 6.49 | 5.28 |
| 40 | 11.06 | 4.61 | 5.18 | 2.18 | 7.87 | 5.09 |
| 60 | 11.36 | 5.22 | 5.13 | 2.32 | 8.11 | 5.21 |
| 80 | 11.90 | 4.98 | 5.27 | 1.95 | 8.22 | 5.62 |
| 60, T4(T8)-PS particles | 11.55 | 5.46 | 5.54 | 2.58 | 8.51 | 6.78 |
| % L in wbc | 24.5 | | 12.5 | | 19.1 | |
| % in L, T4(T8)-Au-PS particles | 46.4 | 21.3 | 41.0 | 18.6 | 4.25 | 27.3 |
| % in L, T4(T8)-PS particles | 47.1 | 22.3 | 44.3 | 20.6 | 44.5 | 35.5 |
| flow % | 45.9 | 25.9 | 55.2 | 24.6 | 43.2 | 35.0 |
| STKS % | 42.3 | 22.5 | 56.2 | 25.0 | 41.3 | 30.4 |

The percentage CD4 or CD8 generally reached a constant value at a titer of 40 $\mu$L of 1% w/v solids particles per 400 $\mu$L of whole blood. This is about twice the minimum titer (iii) SALS versus DC, and (iv) SALS versus RF. Thus, the antibody-conjugated polystyrene particles of this invention can be resolved from antibody-conjugated silver or gold polystyrene particles by a judicious choice of excitation laser wavelength between 450 and 800 nm to excite the plasmon resonances of either silver ($\lambda_{exc}$=400–520 nm) or gold ($\lambda_{exc}$>520 nm) or both colloids ($\lambda_{exc}$=520–800 nm) deposited on the surface of polystyrene particles, and choice of the SALS versus UMALS, DC, or RF and UMALS versus DC matrices.

The wavelength dependence provides a method of using two- or three-color, antibody-conjugated particles, with or without immobilized silver or gold colloids, and different antibodies targeting mutually exclusive white blood cell subsets, to analyze simultaneously for two or three subset populations of white blood cells.

The total light scattering of gold particles of diameter 50 to 200 nm, embedded on the surface of spherical 2 micron diameter polystyrene particles, which surround white blood cells specifically targeted by the antibody-coated particles should be a superposition of three main scattering contributions: (1) cell scatter, (2) polystyrene particle scatter, and (3) gold particle scatter. Since the 2 µm polystyrene particles are generally smaller than white blood cells, their attachment to the surface of cells perturbs the light scatter of the original cells according to the effect of the particle-to-cell ratio and geometrical arrangement of particles around cells on the shape and size of particle-cell conjugates. The gold particles are much smaller than either the polystyrene particles or the white blood cells; therefore, their effect on the shape and size of particle-cell conjugates is negligible. However, because of their particular wavelength-dependent extinction spectra in the visible-near infrared region, the gold particles show additional scattering and absorption that was not present in polystyrene particle-cell conjugates.

Also, the concentration of gold-polystyrene particles on the surface of a cell where the particles become nearest neighbors in close contact to each other can perturb the extinction characteristics of the separated, gold-polystyrene particles. Furthermore, the absorption part of the extinction of gold particles can be substantial and in some angular scattering ranges produces a loss in scattering intensity relative to the scattering from polystyrene particle-cell conjugates.

The additional side scatter shift for antibody-aminotrithiol-Au-Amdex-PS particles attached to lymphocyte subsets was small relative to the shift for PS particles attached to the same cells; however, changes in the position of targeted lymphocytes in SALS versus UMALS matrices allowed a clear separation between antibody-aminotrithiol-Au-Amdex-PS and PS shifted lymphocyte populations due to a substantial decrease in UMALS for cells coated with antibody-aminotrithiol-Au-Amdex-PS particles. Antibody-Amdex-Ag-Amdex-PS particles attached to lymphocytes have the same effect as the antibody-aminotrithiol-Au-Amdex-PS particles themselves, in that forward scatter and UMALS are decreased relative to the scatter of lymphocytes labeled with PS particles. However, side scatter of targeted lymphocytes labeled with antibody-Amdex-Ag-Amdex-PS particles was enhanced about twice as much as the side scatter of lymphocytes labeled with the antibody-aminotrithiol-Au-Amdex-PS particles.

Example 8—Simultaneous Analyses of Lymphocyte Subpopulations

Simultaneous determination of the percentage of CD4 or CD8+ positive cells in a white blood cell population of whole blood was made on a modified Coulter VCS instrument using T4 or T8-conjugated polystyrene and T8 or T4-conjugated, gold- or silver-coated polystyrene particles of this invention.

The particles used contained T4 and T8 antibodies conjugated to gold-coated PS particles, or silver-coated PS particles, and diaminopropane (DAP)-coated PS aldehyde/sulfate particles for the reasons described in Example 7.

Briefly, the conjugates were mixed with whole blood, and then white blood cells were analyzed after an acid lyse of red blood cells and quench. Specifically, 40 µL of 1% w/v solids T4 (T8)-conjugated polystyrene particles and 40–60 µL of T8 (T4)-conjugated, gold- or silver coated polystyrene particles were mixed with 400 µL of whole blood for about 2 minutes. The mixtures were then treated and analyzed as in Example 7.

Representative matrices are shown in FIGS. 14A–14F. The 90° LS versus UMALS matrices showed the best separation of cells labeled with T4(T8)-conjugated polystyrene particles from cells labeled with T8(T4)-conjugated, gold- or silver-coated polystyrene particles. Only cells labeled with T4(T8)-conjugated polystyrene particles were resolved in UMALS versus DC matrices and cells labeled with T4(T8)-conjugated, gold- or silver-coated particles were sometimes resolved in 90° LS versus RF, DC matrices.

Percentage CD4/percentage CD8 in white blood cell were obtained from analyses of 90° LS versus UMALS matrices for mixtures of 60 L T4(T8)-PS/60 L TS(T4)-Au-PS particles with 400 µL of whole blood for three donors in triplicate. Table 3 shows the percentage of CD4/CD8 positive cells in whole blood for three donors.

TABLE III

Percentage CD4, CD8 Positive Cells in Whole Blood

| Donor | 49070 | | 50184 | | 53608 | |
| --- | --- | --- | --- | --- | --- | --- |
| | % CD4 | % CD8 | % CD4 | % CD8 | % CD4 | % CD8 |
| T4-PS/ T8-Au-PS particles | | | | | | |
| Trial 1 | 12.40 | 5.10 | 5.67 | 2.40 | 8.84 | 4.95 |
| Trial 2 | 12.50 | 5.43 | 6.11 | 2.55 | 9.67 | 5.16 |
| Trial 3 | (14.16) | 5.02 | 5.61 | 2.61 | 9.71 | 5.30 |
| Mean | 12.45 | 5.18 | 5.80 | 2.52 | 9.41 | 5.14 |
| 4 min | 13.48 | 5.24 | 5.75 | 2.76 | 9.48 | 4.90 |
| Mean % in L | 50.8 | 21.1 | 46.4 | 20.2 | 49.3 | 26.9 |
| T8-PS/ T4-Au-PS particles | | | | | | |
| Trial 1 | 10.05 | 7.01 | 6.65 | 3.18 | (19.66) | 7.30 |
| Trial 2 | 11.13 | 6.72 | 6.81 | 2.86 | 14.43 | 7.16 |
| Trial 3 | (8.80) | 7.26 | 6.55 | 2.63 | 14.57 | 6.98 |
| Mean | 10.59 | 7.00 | 6.67 | 2.89 | 14.50 | 7.15 |
| 4 min | 10.29 | 6.38 | 6.52 | 2.96 | 13.80 | 7.19 |
| Mean % in L | 43.2 | 28.6 | 53.4 | 23.1 | 75.9 | 37.4 |
| % in L, T4(T8)-PS particles | 47.1 | 22.3 | 44.3 | 20.6 | 44.5 | 35.5 |
| flow % | 45.9 | 25.9 | 55.2 | 24.6 | 43.2 | 35.0 |
| STKS % | 42.3 | 22.5 | 56.2 | 25.0 | 41.3 | 30.4 |

For some runs, adjustment of the gate in the bottom left-hand corner of the matrices to higher 90° LS and higher UMALS can improve the agreement between percentage CD4/CD8 obtained on the modified VCS instrument and the results obtained by flow cytometry. For example, after adjustment for donor 49070, percentage CD4 in L=45.6 with T4-Amdex-PS/T8-aminotrithiol-Au-Amdex-PS particles and percentage CD8 in L=25.6 with T8-Amdex-PS/T4-aminotrithiol-Au-Amdex-PS particles.

For donor 53608, percentage CD4 in L=35.5 with T4-Amdex-PS/T8-aminotrithiol-Au-Amdex-PS particles, percentage CD4 in L=49.7 with T8-Amdex-PS/T4-aminotrithiol-Au-Amdex-PS particles, and percentage CD8 in L=30.6 with T8-Amdex-PS/T4-aminotrithiol-Au-Amdex-PS particles.

Similar results, summarized in Table IV for a single donor, were obtained with 40 μL T4 (T8)-Amdex-PS and 60 μL T8 (T4)-Amdex-Ag-Amdex-PS particles mixed with 400 μL of whole blood and excited with the 633 nm He/Ne laser line, except quantitation against flow comparator data was not as good due to the presence of larger numbers of T4 (T8)-Amdex-Ag-Amdex-PS particle aggregates which broaden the non-targeted cell regions in the various matrices. Table IV shows the percentage of CD4/CD8 positive cells in whole blood using the four different particles.

TABLE IV

Percentage CD4, CD8 Positive Cells in Whole Blood

| | Matrix | % CD4 in L | % CD8 in L |
|---|---|---|---|
| T4-PS or T8-PS particles | 90° LS vs. UMALS | 46.1 | 23.2 |
| | UMALS vs. DC | 37.4 | 21.8 |
| T4-Ag-PS or T8-Ag-PS particles | 90° LS vs. DC | 20.1 | 17.2 |
| T4-PS/T8-Ag-PS particles | UMALS vs. DC | 36.9 | |
| | 90° LS vs. UMALS | | 17.8 |
| T8-PS/T4-Ag-PS particles | 90° LS vs. UMALS | 53.3 | |
| | UMALS vs. DC | | 23.1 |
| | 90° LS vs. DC | 36.9 | |
| | UMALS vs. DC | | 23.1 |
| flow comparator | | 45.6 | 25.4 |

Several gating strategies were used to calculate the percentage of targeted cells in the white blood cell population, one of which is illustrated in FIGS. 15A–15F, for T4-Amdex-PS/T8-aminotrithiol-Au-Amdex-PS particle mixtures. The percentage of lymphocytes in white blood cell was 18.8 for this donor as determined on the COULTER STKS hematology analyzer.

All publications cited in this specification are indicative of the level of skill of those in the art to which this application pertains and are incorporated herein by reference herein.

While the invention has been described with reference to a particularly preferred embodiment, it will be appreciated that modifications can be made without departing from the spirit of the invention. Such modifications are intended to fall within the scope of the appended claims.

What is claimed is:

1. A stable colloidal particle comprising:
   (a) a colloidal-sized core substrate having amine-reactive functional groups thereon;
   (b) an aminodextran coating over the peripheral surface of said substrate;
   (c) a layer of colloidal-sized metallic solid overlaying said aminodextran coating, wherein the metal for said metallic solid is selected from the group consisting of metals which can be reduced from the ionic state to the metal(0) state by the aminodextran coating of said core;
   (d) an aminotrithiolate linker attached to said metallic solid, said linker having a free amino group; and
   (e) a protein attached to said linker by covalently bonding to said free amino group.

2. The particle according to claim 1, wherein said core substrate (a) is polystyrene.

3. The particle according to claim 2, wherein said core substrate (a) ranges in size from between about 0.2 to about 5.0 microns in diameter.

4. The particle according to claim 1, wherein said aminodextran coating (b) is covalently bonded to said core substrate (a) by covalent bonds between the free amino groups of said aminodextran and said amine-reactive functional groups of said substrate.

5. The particle according to claim 4, wherein said aminodextran coating (b) is selected from the group consisting of aminodextrans in which the degree of diamine substitution in said aminodextran is in the range of 1/40–1/35 compared to a maximum theoretical value of 1/2.5.

6. The particle according to claim 5, wherein said diamine substitution in said aminodextran coating (b) is approximately 1/7 to 1/8.

7. The particle according to claim 1, wherein said metallic solid (c) is selected from the group consisting of metals which form metal ions or metal ion complexes which have a reduction potential of +0.7 volts or higher.

8. The particle according to claim 7, wherein said metallic solid is gold.

9. The particle according to claim 7, wherein said metallic solid is silver.

10. The particle according to claim 1 wherein said linker is tris(3-mercaptopropyl)-N-glycylaminomethane.

11. The particle according to claim 1, wherein said aminotrithiolate linker (d) is covalently bonded to said colloidal metal-aminodextran coated substrate by covalent metal-sulfur bonds.

12. The particle according to claim 11 wherein said colloidal metal is gold.

13. The particle according to claim 1, wherein said protein (e) is an antibody.

14. The particle according to claim 13, wherein said antibody is selected from the group consisting of an anti-CD4 antibody and an anti-CD8 antibody.

15. The particle according to claim 1, wherein said protein (e) is covalently bonded to said aminotrithiolate linker-colloidal metal-aminodextran coated substrate by covalent bonding of the free amino groups on the aminotrithiolate linker which are activated with maleimide in sulfo-SMCC, with sulfhydryl groups on the 2-iminothiolane activated protein.

16. The particle according to claim 1 wherein:
   (a) said colloidal-sized core substrate comprises a colloidal-sized polystyrene microparticle;
   (b) said aminodextran coating comprises a 1×-aminodextran coating over the peripheral surface of said polystyrene particle;
   (c) said layer of colloidal-sized metallic solid comprises silver or gold; and
   (d) said protein comprises an anti-CD4 antibody or an anti-CD8 antibody covalently bonded to said free amino group.

17. The particle according to claim 1, which comprises
   (a) a colloidal-sized polystyrene particle;
   (b) a 1×-aminodextran coating over the peripheral surface of said polystyrene particle;
   (c) a layer of colloidal-sized silver overlaying said aminodextran coating;
   (d) a 5×-aminodextran linker having a free amino group; and
   (e) an anti-CD4 antibody attached to said linker by covalently bonding to said free amino group.

18. A method for the simultaneous quantitative determination of two or more subpopulations of white blood cells in a biological solution/suspension containing both red blood cells and white blood cells, said method comprising the steps of:

(a) mixing with said biological solution/suspension, at least two different stable colloidal particles of claim 1, wherein each different particle contains a different said protein which binds to a different epitope on a subpopulation of said white blood cells, said mixing occurring for a time sufficient to permit the binding of said particles to each said subpopulation of cells;

(b) lysing said red blood cells in said biological solution/suspension, and quenching said cells in said mixture (a);

(c) analyzing said mixture of step (b) in an instrument that distinguishes between subpopulations of white blood cells bound by each said different colloidal particles, thereby simultaneously quantitatively enumerating at least two mutually exclusive subpopulations of said white blood cells.

19. The method according to claim 18 wherein said biological fluid is whole blood.

20. The method according to claim 18 wherein the subpopulations are selected from the group consisting of T lymphocytes, B lymphocytes, granulocytes, and monocytes.

21. The method according to claim 20 wherein said lymphocytes are $CD4^+$ lymphocytes and $CD8^+$ lymphocytes.

22. The method according to claim 18 wherein each said protein is an antibody.

23. The method according to claim 18 wherein said instrument distinguishes between cells by light scattering, conductivity and volume.

24. A method of preparing a stable colloidal particle which comprises the steps of:

(a) covalently binding an aminodextran to aldehyde functionalized polystyrene particles to provide aminodextran coated polystyrene particles;

(b) crosslinking additional aminodextran to the particles of step (a) by the use of a selected crosslinking agent and reducing the unstable bonds with a reducing agent;

(c) reacting said aminodextran-coated particles with an excess of metal salt in an aqueous medium at an elevated temperature, in the presence of a second reducing agent, resulting in colloidal metal-aminodextran coated particles;

(d) attaching an aminotrithiolate linker having a free amino group to said colloidal metal-aminodextran coated particles, which linker allows conjugation of proteins to the surface of the metal-colloid coated particles;

(e) activating the amino group of the linker on the colloidal metal-coated particles with a bifunctional crosslinking agent;

(f) activating a selected protein with an amino binding reagent which provides a sulfhydryl group;

(g) purifying each said activated component (e) and (f); and (h) mixing a sufficient amount of an aqueous solution of said activated protein to saturate reactive groups on the particle with an aqueous suspension of said activated particle at room temperature for a sufficient period of time for conjugation between said protein and particle to occur, resulting in a stable colloidal particle.

25. The method according to claim 24, wherein said protein is an antibody.

26. The method according to claim 24, wherein the linker is 5× aminodextran and said metal salt is silver(I).

27. The method according to claim 24, wherein said metal salt is gold(III).

28. The method according to claim 26, wherein said aminodextran linker is attached to said colloidal metal-aminodextran-polystrene particle by adsorption and crosslinking with glutaraldehyde.

29. The method according to claim 27, wherein said linker forms strong covalent bonds between the sulfur groups on the linker and the gold colloid surface.

30. The method according to claim 24 wherein the temperature of step (d) is in the range of between about 80 to about 100° C.

31. The method according to claim 24 wherein the bifunctional crosslinking agent of step (e) which links the aminotrithiol-colloidal metal-aminodextran-polystyrene particle to the protein is sulfosuccinimidyl 4-[N-maleimidomethyl]cyclohexane-1-carboxylate.

32. The method according to claim 24 wherein the binding reagent of step (f) is selected from the group consisting of naturally occurring sulfhydryl groups of the protein, and an amino-reactive sulfhydryl introducing reagent.

* * * * *